United States Patent
Lukman et al.

(10) Patent No.: US 9,977,014 B2
(45) Date of Patent: May 22, 2018

(54) NANOPARTICLE SENSOR FOR NUCLEIC ACID-PROTEIN INTERACTION

(71) Applicant: Agency for Science, Technology and Research, Singapore (SG)

(72) Inventors: Steven Lukman, Singapore (SG); Siu Yee New, Singapore (SG); Xiaodi Su, Singapore (SG); Edwin Chong Wing Cheung, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/275,526

(22) Filed: May 12, 2014

(65) Prior Publication Data

US 2014/0335510 A1 Nov. 13, 2014

(30) Foreign Application Priority Data

May 10, 2013 (SG) .................................. 201303638

(51) Int. Cl.
| | | |
|---|---|---|
| *C12M 1/00* | (2006.01) | |
| *G01N 33/53* | (2006.01) | |
| *G01N 33/543* | (2006.01) | |
| *G01N 33/553* | (2006.01) | |

(52) U.S. Cl.
CPC ... *G01N 33/5308* (2013.01); *G01N 33/54346* (2013.01); *G01N 33/553* (2013.01)

(58) Field of Classification Search
CPC ........... C12Q 1/68; G01N 33/50; C12M 1/34; C07H 21/02; B82Y 15/00
See application file for complete search history.

(56) References Cited

U.S. PATENT DOCUMENTS

| | | | | |
|---|---|---|---|---|
| 6,812,339 B1* | 11/2004 | Venter .................. | C12Q 1/6883 | 435/6.11 |
| 2008/0085508 A1* | 4/2008 | Wei ...................... | G01N 33/587 | 435/5 |

OTHER PUBLICATIONS

Pu et al, Optimizing the cationic conjugated polymer-sensitized fluorescent signal of dye labeled oligonucleotide for biosensor applications, 2009, Biosensors and Bioelectronics, 24, 1067-1073.*
Data sheet New England BioLabs down loaded from the internet (www.neb.com/nebcutter), p. 1 printed on Oct. 6, 2015.*
SEQ ID No. 3 Search results, pp. 1-11, printed on Oct. 7, 2015.*
SEQ ID No. 4 Search results, pp. 1-11, printed on Oct. 7, 2015.*
Pu et al, Optimizing the cationic conjugated polymer-sensitized fluorescent signal of dye labeled oligonucleotide for biosensor applications, 2009, Biosensors and Bioelectronics, 24, 1067-1073, Suppllemental Data, pp. 1-4.*
Song et al, A Simple, Universal Colorimetric Assay for Endonuclease/Methyltransferase Activity and Inhibition Based on an Enzyme-Responsive Nanoparticle System, 2009, ACS NANO, 3, 1183-1189.*
Liu et al, An ultrasensitive label-free biosensor for assaying of sequence-specific DNA-binding protein based on amplifying fluorescent conjugated polymer, 2013, Biosensors and Bioelectronics, 41, 218-224, published Aug. 23, 2012.*
Wang et al, Anionic Conjugated Polymer with Aptamer-Functionalized Silica Nanoparticle for Label-Free Naked-Eye Detection of Lysozyme in Protein Mixtures, 2010, Langmuir, 26(12), 10025-10030.*
Fan et al, Beyond superquenching: Hyper-efficient energy transfer from conjugated polymers to gold nanoparticles, 2003, PNAS, 100, 6297-6301.*
Lukman et al, Hybrid Sensor Using Gold NanopartiCles and Conjugated Polyelectrolytes for Studying Sequence Rule in protein-DNA Interactions, 2013, Appl. Mater. Interfaces, 5, 12725-12734 (post art) (Year: 2013).*
Bajaj, Avinash, et al., "Detection and differentiation of normal, cancerous, and metastatic cells using nanoparticle-polymer sensor arrays", *Proc. Natl. Acad. Sci. USA*, 106(27), (2009), 10912-10916.
Carroll, Jason S., et al., "Chromosome-Wide Mapping of Estrogen Receptor Binding Reveals Long-Range Regulaion Requiring the Forkhead Protein FoxA1", *Cell*, 122, (2005), 33-43.
Chatterjee, Subhasish, et al., "Investigating the distance limit of a metal nanoparticle based spectroscopic ruler", *Biomedical Optics Express*, 2(6), (2011), 1727-1733.
Fang, Jun, et al., "Detection of protein-DNA interaction and regulation using gold nanoparticles", *Analytical Biochemistry*, 399, (2010), 262-267.
Feng, Xuli, et al., "Water-soluble fluorescent congugated polymers and their interactions with biomacromolecules for sensitive biosensors", *Chemical Society Reviews*, 39, (2010), 2411-2419.
Fong, Kah E., et al., "Analysis of metallic nanoparticle-DNA assembly formation in bulk solution via localized surface plasmon resonance shift", *RSC Adv.*, 2, (2012), 5154-5163.
Fong, Kah E., et al., "Head-to-tail: hybridization and single-mismatch discrimination in metallic nanoparticle-DNA assembly", *RSC Adv.*, 3, (2013), 6076-6084.
Frens, G., "Controlled Nucleation for the Regulation of the Particle Size in Monodisperse Gold Suspensions", *Nature*, (1973), 20-22.
Guan, Zhenping, et al., "Enhanced Two-Photon Emission in Coupled Metal Nanoparticles Induced by Conjugated Polymers", *Langmuir*, 26(23), (2010), 18020-18023.
Han, Fei, et al., "Size-Dependent Two-Photon Excitation Photoluminescence Enhancement in Coupled Noble-Metal Nanoparticles", *ACS Applied Materials & Interfaces*, 4, (2012), 4746-4751.
Hornbeck, Paul V., et al., "PhosphoSitePlus: a comprehensive resource for investigating the structure and function of experimentally determined post-translational modifications in man and mouse", *Nucleic Acids Research*, 40, (2012), D261-D270.

(Continued)

*Primary Examiner* — Narayan Bhat
(74) *Attorney, Agent, or Firm* — Schwegman Lundberg & Woessner, P.A.

(57) ABSTRACT

The present invention provides a sensor for sensing nucleic acid-protein interactions, comprising a noble metal nanoparticle (NP), a double stranded nucleic acid molecule capable of binding with a protein in an aqueous solution and a fluorescent conjugated polymer (CP). The present invention also provides a method for sensing nucleic acid-protein interactions with the sensor as defined above.

29 Claims, 17 Drawing Sheets

(56) References Cited

OTHER PUBLICATIONS

Hu, Dong G., et al., "A Novel Polymorphism in a Forkhead Box A1 (FOXA1) Binding Site of the Human UDP Glucuronosyltransferase 2B17 Gene Modulates Promoter Activity and Is Associated with Altered Levels of Circulating Androstane-3α, 17β-diol Glucuronide", *Mol. Pharmacol.*, 78, (2010), 714-722.

Lukman, Steven, et al., "Hybrid assembly of DNA-coated gold nanoparticles with water soluble conjugated polymers for studying protein-DNA interaction and ligand inhibition", *RSC Adv.*, 4, (2004), 8883-8893.

Mirkin, Chad A., et al., "A DNA-based method for rationally assembling nanoparticles into macroscopic materials", *Nature*, 382, (1996), 607-609.

Moyano, Daniel F., et al., "Gold nanoparticle-polymer/biopolymer complexes for protein sensing", *Faraday Discuss.*, 152, (2011), 33-42.

Ou, Li-Juan, et al., "Sensitive and Visual Detection of Sequence-Specific DNA-Binding Protein via a Gold Nanoparticle-Based Colorimetric Biosensor", *Anal. Chem.*, 82, (2010), 6015-6024.

Phillips, Ronnie L., et al., "Rapid and Efficient Identification of Bacteria Using Gold-Nanoparticle-Poly(para-phenyleneethynylene) Constructs", *Angw. Chem. Int. Ed.*, 47, (2008), 2590-2594.

Polavarapu, Lakshminarayana, et al., "Huge enhancement of optical nonlinearities in coupled Au and Ag nanoparticles induced by conjugated polymers", *Applied Physics Letters*, 100, (2012), 023106-1-023106-3.

Rye, Hays S., et al., "Stable fluorescent complexes of double-stranded DNA with bis-intercalating asymmetric cyanine dyes: properties and applications", *Nucleic Acids Research*, 20(11), (1992), 2803-2812.

Shang, Li, et al., "Fluorescent Conjugated Polymer-Stabilized Gold Nanoparticles for Sensitive and Selective Detection of Cysteine", *J. Phys. Chem. C.*, 111, (2007), 13414-13417.

Song, Shiping P., et al., "Functional nanoprobes for ultrasensitive detection of biomolecules", *Chem. Soc. Rev.*, 39, (2010), 4234-4243.

Su, Shao, et al., "Design and applications of gold nanoparticle conjugates by exploiting biomolecule-gold nanoparticle interactions", *Nanoscale*, 5, (2013), 2589-2599.

Tan, Si K., et al., "AP-2γ regulates oestrogen receptor-mediated long-range chromatin interaction and gene transcription", *The EMBO Journal*, 30, (2011), 2569=2581.

Tan, Yen N., et al., "Gold-Nanoparticle-Based Assay for Instantaneous Detection of Transcription Factor-DNA Interactions", *Anal. Chem.*, 82, (2010), 2759-2765.

Tan, Yen N., et al., "Sensing of Transcription Factor through Controlled-Assembly of Metal Nanoparticles Modified with Segmented DNA Elements", *ACS Nano*, 4(9), (2010), 5101-5110.

Tan, Yen N., et al., "Study of Single-Stranded DNA Binding Protein-Nucleic Acids interactions using Unmodified Gold Nanoparticles and Its Application for Detection of Single Nucleotide Polymorphisms", *Anal. Chem.*, 83(11), (2011), 4251-4257.

Wang, Jiasi, et al., "Recent progress in nanosensors for sensitive detection of biomolecules", *Nanoscale*, 5, (2013), 3589-3600.

Wang, Jing, et al., "Fluorescence resonance energy transfer between an anionic conjugated polymer and a dye-labeled lysozymeaptamer for specific lysozyme detection", *Chem. Commun.*, Issue 17, (2009), 2284-2286.

Williams, Trevor, et al., "Analysis of the DNA-binding and activation properties of the human transcription factor AP-2", *Genes Dev.*, 5(4), (1991), 670-682.

Xia, Fan, et al., "Colorimetric detection of DNA, small molecules, proteins, and ions using unmodified gold nanoparticles and conjugated polyelectrolytes", *Proc. Natl. Acad. Sci. USA*, 107(24), (2010), 10837-10841.

Zeng, Shuwen, et al., "A Review on Functionalized Gold Nanoparticles for Biosensing Applications", *Plasmonics*, 6(3), (2011), 491-506.

Zhang, X., et al., "Instantaneous and Quantitative Functionalization of Gold Nanoparticles with Thiolated DNA Using a pH-Assisted and Surfactant-Fee Route.", *J. Am. Chem. Soc.*, 134(17), (2012), 7266-7269.

Zhang, Xu, et al., "Instantaneous and Quantitative Functionalization of Gold Nanoparticles with Thiolated DNA Using a ph-Assisted and Surfactant-Free Route", *Journal of the American Chemical Society*, 134, (2012), 7266-7269.

Zhu, Chunlei, et al., "Water-Soluble Conjugated Polymers for Imaging, Diagnosis, and Therapy", *Chem. Rev.* 112(8), (2012), 4687-4735.

\* cited by examiner

NANOPARTICLE SENSOR FOR NUCLEIC ACID-PROTEIN INTERACTION

CLAIM OF PRIORITY

This application claims the benefit of priority of Singapore Patent Application Serial No. 201303638-9, entitled "A NANOPARTICLE SENSOR FOR NUCLEIC ACID-PROTEIN INTERACTION," filed on May 10, 2013, the benefit of priority of which is claimed hereby, and which is incorporated by reference herein in its entirety.

TECHNICAL FIELD

The present invention generally relates to a sensor for sensing nucleic acid-protein interactions. The present invention also generally relates to a method for detecting nucleic acid-protein interactions.

BACKGROUND

Sequence specific binding between proteins and nucleic acids plays a critical role in cells, such as in regulation of gene expression. Due to its major role in all biological processes, the nucleic acid-protein interaction is considered an important drug target. Characterization of such nucleic acid-protein interactions have been largely dependent on gel mobility shift assays, DNase I footprinting assays, or filter binding assays. Although these assays can detect the sequence specificity of the binding event, they may also require the use of labels, such as dyes or radioactive labels. The use of labels on the probe or the target not only adds multiple and tedious steps to the synthesis of the sensor and the method of detection before the assay is performed, but may also be hazardous to living organisms in the environment. In addition, they are often not accurate in determining the binding affinity between the protein and the DNA.

Surface Plasmon Resonance (SPR) spectroscopy, which is a label-independent technique, has become an alternative to label-dependent techniques for studying nucleic acid-protein interactions. However, SPR spectroscopy is expensive to conduct, requiring highly specialized equipment and costly consumables in order to carry out the measurements. This makes SPR spectroscopy unsuitable for fast and cost-effective screening of nucleic-acid protein interactions. This is particularly important for applications such as screening of drug molecules where fast, cost-effective and efficient screening of a plurality of drugs is necessary. In addition, SPR is limited by the fact that only certain size molecules can be measured for binding-interactions, restricting its utility for measuring a wide range of possible interactions.

Fluorescence anisotropy (FA) is an alternative method for studying nucleic acid-protein interactions and for screening low molecular weight ligand inhibitors for the protein binding to nucleic acids. However, FA, like many other methods based on the use of an organic dye, requires attachment of a fluorophore to small molecules that act as probes or ligands for the protein. This can become an extensive iterative process, involving numerous tests for reactions that may occur at multiples sites on the probe or ligand molecule. Furthermore, the optimization of linker length and position can be both time- and labour-intensive. In addition, problems such as steric hindrance may arise upon addition of the fluorescent group to the probe or ligand, which may affect its affinity for the protein. Some fluorophores may also suffer from low inherent photostability, self-quenching and low quantum yields, or only show high sensitivity within a certain pH range. These drawbacks can make the assay inefficient and ineffective.

There is therefore a need to provide a sensor for nucleic acid-protein interaction which may at least partially ameliorate one or more of the disadvantages described above.

SUMMARY

In a first aspect, there is provided a sensor for sensing nucleic acid-protein interactions, comprising: (a) a noble metal nanoparticle (NP); (b) a first single stranded nucleic acid molecule bonded onto the NP; (c) a second, single stranded nucleic acid molecule, which is partially or completely complementary to the first nucleic acid molecule and is hybridized to the first nucleic acid molecule, to form a double stranded nucleic acid molecule capable of binding with a protein in an aqueous solution; and (d) an enhanceable or quenchable fluorescent conjugated polymer (CP).

Advantageously, the disclosed sensor may sense nucleic acid-protein interactions. The sensor may be able to determine the presence or absence of nucleic acid-protein interactions, quantify the $K_d$ of the nucleic acid-protein interaction or quantify the mole ratio of the nucleic acid-protein interaction. Advantageously, the sensor may comprise a double stranded nucleic acid molecule bonded onto a NP. The protein may interact with the double stranded nucleic acid molecule. Further advantageously the probe for detecting nucleic acid-protein interaction may be a double stranded nucleic acid molecule. Advantageously, the sensor may sense the interaction between the double stranded nucleic acid molecule and a protein that binds to double stranded nucleic acid. More advantageously, the double stranded nucleic acid molecule may comprise a protein recognition sequence which may facilitate the binding of a protein to the nucleic acid molecule.

Advantageously, the disclosed sensor may be simple, rapid and sensitive at sensing nucleic acid-protein interaction. More advantageously, the sensor may be more sensitive than conventional methods such as EMSA and FA for detecting nucleic acid-protein interactions. Further advantageously, the sensor may not require complex, tedious and often hazardous modifications such as radio-labelling or dye-labelling on the nucleic acid. More advantageously, the sensor may not require modification of the protein.

Advantageously, the disclosed sensor may sense nucleic acid-protein interactions using fluorescence as the output signal. Advantageously, the use of hazardous output signals such as radiation may not be required. Advantageously, the disclosed sensor may comprise fluorescent, water-soluble conjugated polymers (CPs). CPs may be promising materials for biosensing and imaging due to their unique electrical and optical properties. Advantageously, the disclosed sensor may utilize CPs that have excellent fluorescent properties. CPs may be capable of interacting with multiple targets due to its size, making them efficient fluorophores for use in the disclosed sensor. Further advantageously, CPs may produce a collective response that may enhance the sensitivity of the sensor. Further advantageously, the CPs may not photobleach or self-quench. Advantageously, these properties may be attributed to the delocalized electron structure which may facilitate efficient energy/electron transport over long distances. More advantageously, CPs may be introduced to the sensor independently of the protein or the nucleic acid. That is, the CP may not require to be conjugated to the nucleic acid-protein, NP or any other component of the sensor.

More advantageously, the CPs may be a conjugated polyelectrolyte (CPE) that has ionizable side groups. Advantageously, this may allow the CP to be anionic or cationic, making them suitable for sensing proteins of different charges. More advantageously, the CPs may be water-soluble by virtue of their charges, making them suitable for use in bioassays where the solvent is an aqueous solution. Advantageously, the CPE may couple optoelectronic/redox properties of the conjugated backbone with solubility in polar solvents and processability due to the ionic solubilizing groups. More advantageously, CPEs may be amphiphilic due to their hydrophobic backbone and hydrophilic side group, making them useful for simultaneously interacting with proteins, nucleic acids, NPs or any mixture thereof. Further advantageously, CPEs may not be significantly pH-sensitive. These properties of the CPEs make them useful as the fluorescent donor for the sensing of nucleic acid-protein interaction in the disclosed sensor.

Advantageously, the disclosed sensor may comprise nanoparticles (NPs). NPs may have unique optical properties arising from their ability to support localized surface plasmon resonance (LSPR). Advantageously, NPs may be suitable for use as part of a fluorimetric sensor due to their ability to enhance fluorescence of proximal fluorophores. More advantageously, the fluorescence enhancement may be due to metal enhanced fluorescence (MEF). Advantageously, NPs may be suitable for use as part of a fluorimetric sensor due to their ability to super quench proximal fluorophores. Advantageously, the sensor may utilize the super quenching properties of NPs. More advantageously, NPs may be capable of super quenching the fluorescence of water soluble CPs. The super quenching abilities may be due to Foerster Resonance Energy Transfer (FRET) or Nanoparticle Surface Energy transfer (NSET). Advantageously, the sensing of the nucleic acid-protein interaction may be dependent on the relative distance, orientation and spectral overlap between the NP and the CP. Further advantageously, the sensor may allow the use of a variety of CPs as a fluorescence donor due to the broad absorption spectrum and high extinction coefficient of the NP fluorescence acceptor. More advantageously, the size, shape and dimensionality of the NPs may give NPs a higher surface area than conventional fluorescence quenchers for increased ease, speed and sensitivity for sensing nucleic acid-protein interactions.

Advantageously, the disclosed sensor may facilitate the modulation of CP fluorescence as a result of protein binding to the double stranded nucleic acid bonded onto the NP. Further advantageously, this modulation in fluorescence may be used as a clear optical signal to determine the presence or absence of binding of the protein to the nucleic acid. Further advantageously, the sensor may exploit the combination of the excellent fluorescence properties of CPs and high extinction coefficient of NPs. More advantageously, the interplay between the CPs and NPs may make the sensor versatile for sensing a variety of nucleic acid-protein interactions. Further advantageously, the interplay between the CPs and NPs may be modulated to tune the property of the sensor. This may allow sensing of variety of proteins both of known and unknown charge properties. More advantageously, a small change in the charge of the nucleic acid bonded onto the NP as a result of nucleic acid-protein interaction may cause a change in the fluorescence signal. Further advantageously, this change in fluorescence signal may be amplified by virtue of the nature of the sensor, increasing the sensitivity of the sensor.

Advantageously, the disclosed sensor may detect sequence specific nucleic acid-protein binding for proteins of known or unknown charge properties. Advantageously, the fluorescence of the CP may be quenched when it is in contact with the NP onto which the double stranded nucleic acid is bonded. When contacted with a protein of interest, the fluorescence of the CP may become increased (restored) or decreased (further quenched). This modulation in fluorescence may be due to the binding of the protein of interest to the double stranded nucleic acid molecule. Advantageously, the binding of the protein to the double stranded nucleic acid molecule bonded onto the NP may change the energy/electron transfer properties between the CP and the NP, causing the modulation in fluorescence. This modulation in fluorescence may be dependent on the relative charges of the CP and the protein of interest. The modulation in fluorescence may be fluorescence restoration or further quenching. Advantageously, both fluorescence restoration and further quenching may be used to study nucleic acid-protein interaction between nucleic acid and proteins with different charges. Advantageously, an appropriate combination of CPs and NP, to allow an intermediate fluorescence quenching of the CP prior to protein detection, may be desirable since it may facilitate dual-sensing of both positive and negative proteins.

Advantageously, the disclosed sensor may be used for sensing nucleic acid-protein interactions. Further advantageously, the disclosed sensor may be used in an assay kit for sensing nucleic acid-protein interactions.

In a second aspect, there is provided a method for sensing nucleic acid-protein interactions comprising the steps of: (i) bringing an aqueous solution suspected to comprise or known to comprise a protein of interest with the sensor as defined above; and (ii) detecting the presence or absence of a fluorescent signal to determine the nucleic acid-protein binding.

Advantageously, the disclosed method may be a "mix-and-read" assay, which may be simple, rapid and sensitive. Unlike surface plasmon resonance (SPR), the method may not require any bulky and expensive equipment or consumables. Unlike gel electrophoretic mobility assays, the method may circumvent the use of radioisotopes that are hazardous to organisms in the environment and tedious filtration or separation steps. Further advantageously, the method may circumvent the conventional potentially hazardous, labor- and time-intensive steps of labelling the nucleic acid or target protein with radio-isotopes or dyes. Thus, fewer reagents may be needed. More advantageously, unlike conventional methods, the equilibrium between the nucleic acid-protein interaction may not be disturbed during the method as there are no separation steps involved. Further advantageously, repetitively measurements of the output signal are possible, as the method does not destroy the samples or destroy the fluorophore.

Further advantageously, the method may facilitate simple, rapid and sensitive determination of the presence or absence of nucleic acid-protein interactions, the nucleic acid-protein binding constant and binding stoichiometry (n) between the protein and the nucleic acid. More advantageously, the method may allow the screening of protein affinity to a particular nucleic acid sequence.

Advantageously, the disclosed method may also be used to determine the effect of ligand binding to the nucleic acid-protein interaction. Unlike conventional methods, the disclosed method may not be constrained by the size, shape or the molecular weight of the ligand. Further advantageously, the disclosed method may facilitate rapid screening of the effect of both positive ligands and negative ligands on the nucleic acid-protein interaction. More advantageously, the disclosed method may facilitate detection of a wider range of nucleic acid-protein interactions by virtue of its properties. Further advantageously, establishing the characteristics of sequence specific nucleic acid-protein interactions and ligand inhibition may be important in biomedical research.

In a third aspect, there is provided a method for sensing nucleic acid-protein interactions, comprising the steps of:
(i) bringing an aqueous solution suspected to comprise or known to comprise a protein of interest with a sensor comprising;
   a. a noble metal nanoparticle (NP);
   b. a single stranded nucleic acid molecule capable of binding with a protein in an aqueous solution bonded onto the NP; and
   c. an enhanceable or quenchable fluorescent conjugated polymer (CP); and
(ii) detecting the presence or absence of a fluorescent signal to determine the nucleic acid-protein binding.

Advantageously, the method for sensing nucleic acid-protein interactions may facilitate sensing of nucleic-acid protein interactions that occur between a single stranded nucleic acid molecule and a protein that binds to a single stranded nucleic acid molecule.

Advantageously, the disclosed method may be used in an assay for sensing nucleic acid-protein interactions.

Definitions

The following words and terms used herein shall have the meaning indicated:

The term "inert", for the purposes of this disclosure, refers to metals that are resistant to corrosion and oxidation.

The terms "biologically inert" or "bioinert" may be used interchangeably and refer to materials that do not initiate a response or interact when introduced to biological tissue. That is, introducing the material to the body will not cause a reaction with the host.

The term "nanoparticle" refers to a small object that behaves as a whole unit with respect to its properties. For the purposes of this disclosure, a nanoparticle refers to a particle that covers a range between about 1 nm and about 250 nm. Nanoparticles may or may not exhibit size-related properties that differ significantly from those observed in fine particles or bulk materials. The nanoparticle may have different shapes, including but not limited to spheres, discs, rods, fibers, cups, boxes, pyramids, tetrahedron, octahedron, decahedron, tetrapods, multipods, stars, and the like.

The term "bonded onto" for the purposes of this disclosure, refers to a chemical bond formed between a nucleic acid molecule and the surface of a nanoparticle.

The term "nucleic acid molecule" refers to a molecule made from one or more nucleotide monomers. The nucleic acid molecule may be single stranded (ss) or double stranded (ds). Nucleic acid molecules may include, but are not limited to, deoxyribonucleotide (DNA), ribonucleic acid (RNA), small interfering RNA (siRNA), peptide nucleic acid (PNA), locked nucleic acid (LNA) and the like.

The term "complementary" for the purposes of this disclosure in reference to nucleic acid molecules refers to the distinct interactions between nucleobases. Nucleobases may be any one of adenine (A), thymine (T), uracil (U), guanine (G), cytosine (C) or derivatives thereof. For example, in DNA, adenine is complementary to thymine and guanine is complementary to cytosine, while in RNA, adenine is complementary to uracil and guanine is complementary to cytosine. The term "complimentarity" should be construed accordingly.

The term "protein" refers to a large molecule comprising one or more chains of amino acids. The protein may further comprise of components made up of nucleotides. The protein may be negatively charged or positively charged. The protein may have a vast array of functions, including but not limited to, catalysis, gene regulation, responding to stimuli and the like.

The terms "artificial protein" and "synthetic protein" may be used interchangeably, and refer to man-made molecules that mimic the function and structure of naturally occurring proteins. An artificial protein may have genetic sequences that are not seen in naturally occurring proteins. An artificial protein may bind to specific recognition sequences.

The term "conjugated polymer" refers to polymeric organic macromolecules which consist at least of one backbone chain of alternating single- and multiple- (double- or triple-) bonds.

Conjugated polymers have regions of overlapping p-orbitals, bridging the interjacent single bonds. This allows delocalization of pi electrons across all the adjacent aligned p-orbitals.

The term "charged" for the purposes of this disclosure in reference to proteins, refers to the protein having a net positive charge or a net negative charge. The net charge of the protein may depend on the relative pH of the solvent to the isoelectric point (pI) of the protein. If pH>pI, then the protein will have a net positive charge. If pI<pH, then the protein will have a net negative charge.

The term "recognition sequence" refers to a nucleic acid sequence or subset thereof, to which the nucleic-acid binding domain motif of a protein is specific to. That is, the recognition sequence is a nucleic acid sequence that a protein has specificity for. A particular protein may have specificity for a particular nucleic acid sequence, which is the recognition sequence for that particular protein.

The term "enhance" in reference to fluorescence for the purposes of this disclosure, refers to any process that increases the fluorescence intensity of a given substance. Enhancement may be a result of, but not limited to, excited state reactions, energy transfer, electron transfer, complex formation, colloidal quenching and the like. Enhancement may be static or dynamic. The term "enhanceable" should be construed accordingly.

The term "quench" in reference to fluorescence for the purposes of this disclosure, refers to any process that decreases the fluorescence intensity of a given substance. Quenching may be a result of, but not limited to, excited state reactions, energy transfer, electron transfer, complex formation, colloidal quenching and the like. Quenching may be static or dynamic. The term "quenchable" should be construed accordingly.

The terms "restore" and "recover" in reference to fluorescence for the purposes of this disclosure, may be used interchangeably, and refer to the increase in fluorescence following initial quenching. The terms "restoration" and "recovery" should be construed accordingly.

The term "ligand", for the purposes of this disclosure, refers to small molecules that may bind to proteins. The ligand may be a positive ligand or a negative ligand. A positive ligand refers to a ligand that can inhibit protein binding to nucleic acid, while a negative ligand is a ligand that does not inhibit the binding. A ligand may bind strongly (with high affinity) to a certain protein but not inhibit the subsequent protein binding to nucleic acid and vice versa.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the terms "about" and "approximately", in the context of concentrations of components of the formulations, or where applicable, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF OPTIONAL EMBODIMENTS

A sensor for sensing nucleic acid-protein interactions, may comprise: (a) a noble metal nanoparticle (NP); (b) a first single stranded nucleic acid molecule bonded onto the NP; (c) a second, single stranded nucleic acid molecule, which is partially or completely complementary to the first nucleic acid molecule and is hybridized to the first nucleic acid molecule, to form a double stranded nucleic acid molecule capable of binding with a protein in an aqueous solution; and (d) an enhanceable or quenchable fluorescent conjugated polymer (CP).

A sensor may be any one of a device, detector or converter. A sensor may measure a physical quantity and convert it to a signal that can be read by an observer or an instrument. A sensor may respond to an input quantity by generating a functionally related output in the form of an electrical or optical signal.

Nucleic acid-protein interactions may be any interaction between a nucleic acid and a protein. The interaction may be a physical force. The interaction may be attraction or repulsion. The interaction may be any one of electrostatic interaction, salt bridge interaction, dipolar interaction, dipole-dipole interaction, ion-dipole interaction, hydrogen bonding, entropic interaction, hydrophobic interaction, dispersion forces or base stacking. The interaction may be a sequence-specific interaction or a non-sequence specific interaction.

The sensor may comprise a noble metal nanoparticle (NP).

The sensor may comprise a microparticle or an NP. The microparticle may have a size in the range of any one of about 2,500 nm to about 10,000 nm or about 100 nm to about 2,500 nm. The NP may be a small object that behaves as a whole unit. The NP may be any one of a coarse NP, fine NP or ultrafine NP. The NP may have a size in the range of about 5 nm to about 200 nm, about 5 nm to about 10 nm, about 5 nm to about 15 nm, about 5 nm to about 50 nm, about 5 nm to about 70 nm, about 5 nm to about 80 nm, about 5 nm to about 100 nm, about 5 nm to about 150 nm, about 10 nm to about 15 nm, about 10 nm to about 50 nm, about 10 nm to about 70 nm, about 10 nm to about 80 nm, about 10 nm to about 100 nm, about 10 nm to about 150 nm, about 10 nm to about 200 nm, about 15 nm to about 50 nm, about 15 nm to about 70 nm, about 15 nm to about 80 nm, about 15 nm to about 100 nm, about 15 nm to about 150 nm, about 15 nm to about 200 nm, about 50 nm to about 70 nm, about 50 nm to about 80 nm, about 50 nm to about 100 nm, about 50 nm to about 150 nm, about 50 nm to about 200 nm, about 70 nm to about 80 nm, about 70 nm to about 100 nm, about 70 nm to about 150 nm, about 70 nm to about 200 nm, about 80 nm to about 100 nm, about 80 nm to about 150 nm, about 80 nm to about 200 nm, about 100 nm to about 150 nm, about 100 nm to about 200 nm or about 150 nm to about 200 nm. The NP may have a size in the range of about 10 nm to about 70 nm or about 80 nm to about 200 nm.

The NP may be a nanocluster. A nanocluster may have at least one dimension in the range of about 1 nm to about 10 nm. The NP may be a nanopowder. The nanopowder may be an agglomerate of ultrafine particles, NPs or nanoclusters. The NP may be a nanocrystal. The nanocrystal may be a nanometer-sized single crystal or a single-domain ultrafine particle. The NP may be homogeneous or heterogeneous. The NP size may be uniform or non-uniform. The NP may or may not exhibit size-related properties that differ significantly from those observed in fine particles or bulk materials. The NP may have different shapes. The shape of the NP may be selected from any one of spheres, discs, rods, fibers, cups, boxes, pyramids, tetrahedron, octahedron, decahedron, tetrapods, multipods, or stars. The NP may be a sphere. The NP may or may not exhibit shape-related properties.

The NP may have a diameter in the range of any one of about 5 nm to about 200 nm, about 5 nm to about 10 nm, about 5 nm to about 15 nm, about 5 nm to about 50 nm, about 5 nm to about 70 nm, about 5 nm to about 80 nm, about 5 nm to about 100 nm, about 5 nm to about 150 nm, about 10 nm to about 15 nm, about 10 nm to about 50 nm, about 10 nm to about 70 nm, about 10 nm to about 80 nm, about 10 nm to about 100 nm, about 10 nm to about 150 nm, about 10 nm to about 200 nm, about 15 nm to about 50 nm, about 15 nm to about 70 nm, about 15 nm to about 80 nm, about 15 nm to about 100 nm, about 15 nm to about 150 nm, about 15 nm to about 200 nm, about 50 nm to about 70 nm, about 50 nm to about 80 nm, about 50 nm to about 100 nm, about 50 nm to about 150 nm, about 50 nm to about 200 nm, about 70 nm to about 80 nm, about 70 nm to about 100 nm, about 70 nm to about 150 nm, about 70 nm to about 200 nm, about 80 nm to about 100 nm, about 80 nm to about 150 nm, about 80 nm to about 200 nm, about 100 nm to about 150 nm, about 100 nm to about 200 nm or about 150 nm to about 200 nm. The NP may have a diameter in the range of about 10 nm to about 70 nm or about 80 nm to about 200 nm.

The sensor may comprise a metal NP. The metal may be any one of an alkali metal, alkaline earth metal, transition metal, post-transition metal, lanthanide metal, actinide metal or any alloy thereof. The metal may be a transition metal or any alloy thereof. The metal may be any one of a group 8 transition metal, group 9 transition metal, group 10 transition metal, group 11 transition metal, group 12 transition metal, group 13 transition metal or any alloy thereof. The metal may be any one of a group 8 transition metal, group 10 transition metal, group 11 transition metal or any alloy thereof.

The metal may be chemically or biologically inert. The metal may be resistant to corrosion or oxidation. The metal may be a noble metal. The noble metal may not readily undergo corrosion or oxidation. The metal may be any one of ruthenium (Ru), rhodium (Rh), palladium (Pd), silver (Ag), osmium (Os), iridium (Ir), platinum (Pt), gold (Au) or any alloy thereof. The metal may be a biologically inert metal. The metal may not initiate a response or undergo chemical reactions when introduced to biological tissue. The metal may be any one of ruthenium (Ru), platinum (Pt), silver (Ag), gold (Au) or any alloy thereof. The metal may be Au.

The sensor may comprise a noble metal NP. The sensor may comprise a gold (Au) NP (AuNP).

The AuNP has unique optical and electronic properties. The interaction of AuNPs with light is strongly dictated by their environment, size and physical dimensions. Oscillating electric fields of a light ray may propagating near a colloidal nanoparticle may interact with free electrons, causing a concerted oscillation of electron charge that is in resonance with the frequency of light. These resonant oscillations, known as plasmons, may depend on the size of the NP. For small monodisperse (~30 nm) AuNPs, the surface plasmon resonance phenomena may cause an absorption of light in the blue-green portion of the spectrum (~450 nm) while red light (~700 nm) may be reflected. As particle size increases, the wavelength of surface plasmon resonance related absorption shifts to longer wavelengths. Red light is then absorbed and blue light is reflected. The surface plasmon resonance may be tuned by varying the size or shape of the NP, leasing to particles with tailored optical properties for different applications.

The sensor may comprise a first single stranded nucleic acid molecule bonded onto the NP. The first single stranded nucleic acid molecule may be selected from the group consisting of any one of deoxyribonucleic acid (DNA), ribonucleic acid (RNA), small interfering RNA (siRNA), peptide nucleic acid (PNA) and locked nucleic acid (LNA).

The first single stranded nucleic acid molecule may be modified at the 3'-end or at the 5'-end with a chemically reactive functional group. The chemically reactive functional group may be any one of a thiol, alcohol, amine, azide, alkyne, or biotin. The chemically reactive functional group may be reacted with the NP to form a chemical bond. The single stranded nucleic acid molecule may be chemically bonded onto the surface of the NP. The chemical bond may be a covalent bond.

The first single stranded nucleic acid molecule may be covalently bonded onto the NP. The covalent bond may be selected from the group consisting of any one of thiol, cyclic disulfide, —S—, —S(O)—, —S(O)$_2$—, —S—S—, —O—, —NH$_2$—, —CH$_2$—, —CO$_2$, —N(Me)—, —N(Ac)—, —CONH—, —NHCO—, —NHCONH—, —S(O)$_2$NH—, —NHS(O)$_2$— and —NHS(O)$_2$NH—. The first nucleic acid molecule may be covalently bonded onto the NP through one or more sulfur groups. The covalent bond may be any one of an alkanethiol, acyclic disulphide, cyclic disulphide or other types of multidentate thiolated anchor groups. The covalent bond may be a thiolated-gold (S—Au) bond.

The sensor may comprise a second, single stranded nucleic acid molecule, which is partially complementary or completely complementary to the first nucleic acid molecule and is hybridized to the first nucleic acid molecule, to form a double stranded nucleic acid molecule capable of binding with a protein in an aqueous solution.

The second single stranded nucleic acid molecule may be selected from the group consisting of any one of deoxyribonucleic acid (DNA), ribonucleic acid (RNA), small interfering RNA (siRNA), peptide nucleic acid (PNA) and locked nucleic acid (LNA).

Complementarity may be achieved by distinct interactions between nucleobases. The nucleobase may be a purine or pyrimidine. The nucleobases may be any one of adenine, thymine, uracil, guanine, cytosine or derivatives thereof. The purine may be any one of adenine, guanine or derivatives thereof. The pyrimidine may be uracil, cytosine, thymine or derivatives thereof. Purines and pyrimidines may complement each other. Purines and pyrimidines may only base pair with the opposing type of nucleobase. Complementary base pairs may be any one of adenine and thymine, guanine with cytosine or adenine with uracil. A complementary strand of DNA, RNA, siRNA, PNA and LNA may be constructed based on nucleobase complementarity.

The second, single stranded nucleic acid molecule may be partially complementary or completely complementary to the first single stranded nucleic acid molecule. The second single stranded nucleic acid molecule may be completely complementary to the first nucleic acid molecule. The completely complementary second single stranded nucleic acid may have the same number of nucleobases as the first single stranded nucleic acid molecule. Each nucleobase of the completely complementary second single stranded nucleic acid molecule may be a complementary base to a nucleobase of the first single stranded nucleic acid molecule. The completely complementary second single stranded nucleic acid molecule may not have any mismatch bases with the first single stranded nucleic acid molecule.

The partially complementary second single stranded nucleic acid may have the same number of nucleobases or different numbers of nucleobases as the first single stranded nucleic acid. The partially complementary second single stranded nucleic acid may have more nucleobases or less nucleobases than the first single stranded nucleic acid. Some of the nucleobases of the partially complementary second single stranded nucleic acid molecule may be a complementary base to a nucleobase of the first single stranded nucleic acid molecule. The partially complementary second single stranded nucleic acid molecule may have any mismatch bases with the first single stranded nucleic acid molecule.

The first single stranded nucleic acid molecule may be hybridized to the second single stranded nucleic acid molecule. The hybridization may be sequence-specific or non-sequence specific.

The sensor may comprise a double stranded nucleic acid molecule. The sensor may comprise a double stranded nucleic acid molecule having a first single stranded nucleic acid molecule which is partially complementary or completely complementary to the first nucleic acid molecule. The double stranded nucleic acid molecule may comprise a first single stranded nucleic acid molecule that is completely hybridized or partially hybridized with the second single stranded nucleic acid molecule. The double stranded nucleic acid molecule may partially comprise a single stranded nucleic acid sequence. Any one of the 5'-end, 3'-end or both ends of the double stranded nucleic acid molecule may be a single stranded nucleic acid sequence. The double stranded nucleic acid molecule may comprise a complementary base pair sequence and a single stranded nucleic acid sequence. The double stranded nucleic acid sequence may comprise single stranded nucleic acid hanging off any one of the 5'-end, 3' end or both ends.

The double stranded nucleic acid molecule may be a double helix. The double stranded nucleic acid molecule may further comprise any one of a loop, tetraloop, stemloop, hairpin loop, junction, bulge, pseudoknot or internal loop. The double stranded nucleic acid molecule may be a self-complementary nucleic acid molecule.

The sensor may comprise a triple stranded nucleic acid molecule. The triple stranded nucleic acid molecule may be a triple helix. The triple stranded nucleic acid molecule may further comprise a third, single stranded nucleic acid molecule, which is partially complementary or completely complementary to the double stranded nucleic acid molecule, to form a triple stranded nucleic acid molecule capable of binding with a protein in an aqueous solution. The sensor may comprise a quadruple stranded nucleic acid molecule. The quadruple stranded nucleic acid molecule may be a G-quadruplex. The quadruple stranded nucleic acid molecule may further comprise a fourth, single stranded nucleic acid molecule, which is partially complementary or completely complementary to the triple stranded nucleic acid molecule, to form a quadruple stranded nucleic acid molecule capable of binding with a protein in an aqueous solution.

The sensor may have a mole ratio of double stranded nucleic acid:NP in the range of any one of about 90:1 to about 100:1, about 90:1 to about 92:1, about 90:1 to about 94:1, about 90:1 to about 96:1, about 90:1 to about 96:1, about 90:1 to about 98:1, about 92:1 to about 94:1, about 92:1 to about 96:1, about 92:1 to about 96:1, about 92:1 to about 98:1, about 92:1 to about 100:1, about 94:1 to about 96:1, about 94:1 to about 98:1, about 94:1 to about 100:1, about 96:1 to about 98:1, about 96:1 to about 100:1 or about 98:1 to about 100:1.

The NP onto which the double stranded nucleic acid molecule is bonded may absorb UV-Vis radiation. The NP onto which the double stranded nucleic acid molecule is bonded may absorb UV-Vis radiation in the range of any one of about 200 nm to about 800 nm, about 200 nm to about 300 nm, about 200 nm to about 400 nm, about 200 nm to about 500 nm, about 200 nm to about 600 nm, about 200 nm to about 700 nm, about 300 nm to about 400 nm, about 300 nm to about 500 nm, about 300 nm to about 600 nm, about 300 nm to about 700 nm, about 400 nm to about 500 nm, about 400 nm to about 600 nm, about 400 nm to about 700 nm, about 500 nm to about 600 nm, about 500 nm to about 700 nm or about 600 nm to about 700 nm. The NP onto which the double stranded nucleic acid molecule is bonded may absorb UV-Vis radiation in the range of about 400 nm to about 700 nm. The NP onto which the double stranded nucleic acid molecule is bonded may have a UV-Vis absorption maximum in the range of about 400 to about 700 nm.

The protein may be negatively charged or positively charged. The protein may interact with a nucleic acid. The protein may be a nucleic acid binding protein. The protein may be any one of a transcription factor, polymerase, nuclease, histone, enzyme, chromosome, single stranded DNA binding protein (SSB), ribosome or artificial protein.

The protein may comprise a nucleic acid-binding domain. The protein may comprise any one of a basic helix-turn-helix motif, zinc finger motif, leucine zipper motif, winged helix motif, winged helix turn helix motif, HMG-box motif, Wor3 domain motif or any mixture thereof. The protein may bind to the nucleic acid by a nucleic acid-binding domain. The protein may bind to the nucleic acid by any one of a basic helix-turn-helix motif, zinc finger motif, leucine zipper motif, winged helix motif, winged helix turn helix motif, HMG-box motif, Wor3 domain motif or any mixture thereof. The protein may be a transcription factor. The protein may be a transcription factor involved in the estrogen signalling pathway. The transcription factor may be any one of FoxA1, AP-2γ, ERα, ERβ or SP1. The nucleic acid binding protein may be any one of FoxA1, AP-2γ, ERα, ERβ, or SP1.

FoxA1 and AP-2γ may be TFs in the estrogen signalling pathway that may function as pioneer transcription factors in determining the binding, chromatin-looping, and gene transcription mediated by Estrogen Receptor α (Erα). A detailed characterization of the DNA binding properties of FoxA1 and AP-2γ may therefore be of great importance to understanding how these factors may regulate the transcriptional activity of the estrogen receptor. Identification of small ligand inhibitors for these two TFs may aid in the discovery of alternative drugs for breast cancer therapy.

The double stranded nucleic acid molecule may comprise a protein recognition sequence. The protein recognition sequence may be sequence-specific or non-sequence specific. The recognition sequence may be recognised by one or more proteins. The protein recognition sequence may be any one of a transcription factor recognition sequence, polymerase recognition sequence, nuclease recognition sequence, histone recognition sequence, SSB recognition sequence, ribosome recognition sequence, chromosome recognition sequence or artificial protein recognition sequence.

The protein recognition sequence may be a transcription factor recognition sequence. The transcription factor recognition sequence may be The sensor according to claim 18, wherein the protein recognition sequence may be 5'-GTACTGTAAATAAAACT-3' (SEQ ID NO:3) hybridized to 5'-AGTTTTATTTACAGTAC-3' (SEQ ID NO:4) or 5'-AAAGTGCCCAGAGCCCATG-3 (SEQ ID NO:7) hybridized to 5'-CATGGGCTCTGGGCACTTT-3' (SEQ ID NO:8).

5'-GTACTGTAAATAAAACT-3' (SEQ ID NO:3) hybridized to 5'-AGTTTTATTTACAGTAC-3' (SEQ ID NO:4) may be a transcription factor recognition sequence for FOxA1. 5'-AAAGTGCCCAGAGCCCATG-(SEQ ID NO:7) hybridized to 5'-CATGGGCTCTGGGCACTTT-3' (SEQ ID NO:8) may be a transcription factor recognition sequence for AP-2γ.

The double stranded nucleic acid may have a sequence in the range of any one of about 5 base pairs (bp) to about 100 base pairs (bp), about 5 bp to about 10 bp, about 5 bp to about 15 bp, about 5 bp to about 20 bp, about 5 bp to about 25 bp, about 5 bp to about 50 bp, about 5 bp to about 75 bp, about 10 bp to about 15 bp, about 10 bp to about 20 bp, about 10 bp to about 25 bp, about 10 bp to about 50 bp, about 10 bp to about 75 bp, about 10 bp to about 100 bp, about 15 bp to about 20 bp, about 15 bp to about 25 bp, about 15 bp to about 50 bp, about 15 bp to about 75 bp, about 15 bp to about 100 bp, about 20 bp to about 25 bp, about 20 bp to about 50 bp, about 20 bp to about 75 bp, about 20 bp to about 100 bp, about 25 bp to about 50 bp, about 25 bp to about 75 bp, about 25 bp to about 100 bp, about 50 bp to about 75 bp, about 50 bp to about 100 bp or about 75 bp to about 100 bp. The double stranded nucleic acid may have a sequence in the range of about 15 base pairs (bp) to about 20 base pairs (bp)

The aqueous solution may be a solution that has a solvent that is water. The aqueous solution may be water. The aqueous solution may be a buffer solution. The buffer solution may be a biological buffer solution. The buffer may be any one of a PBS buffer, Tris buffer, Tricine buffer, HEPES buffer, TES buffer, MOPS buffer, PIPES buffer, cacodylate buffer, SSC buffer, MES buffer, Bicine buffer, TAPS buffer or any mixture thereof. The buffer solution may be a HEPES buffer solution. The HEPES buffer solution may have a concentration in the range of any one of about 1 mM to about 100 mM, about 1 mM to about 2 mM, about 1 mM to about 5 mM, about 1 mM to about 10 mM, about 1 mM to about 50 mM, about 2 mM to about 5 mM, about 2 mM to about 10 mM, about 2 mM to about 50 mM, about 2 mM to about 100 mM, about 5 mM to about 10 mM, about 5 mM to about 50 mM, about 5 mM to about 100 mM, about 10 mM to about 50 mM, about 10 mM to about 100 mM or about 50 mM to about 100 mM.

The aqueous solution may have a physiological pH. The aqueous solution may have a physiological pH in the range of pH about 7.0 to about 7.4. The aqueous solution may have a pH in the range of any one of about 5.5 to about 9.5, about 5.5 to about 6.5, about 5.5 to about 7.5, about 5.5 to about 8.5, about 6.5 to about 7.5, about 6.5 to about 8.5, about 6.5 to about 9.5, about 7.5 to about 8.5, about 7.5 to about 9.5 or about 8.5 to about 9.5. The aqueous solution may have a pH in the range of about 6.5 to about 8.5.

The sensor may comprise a conjugated polymer (CP). The CP may be soluble in aqueous solution. The CP may be fluorescent. The CP may emit fluorescence in the range of any one of about 200 nm to about 800 nm, about 200 nm to about 300 nm, about 200 nm to about 400 nm, about 200 nm to about 500 nm, about 200 nm to about 600 nm, about 200 nm to about 700 nm, about 300 nm to about 400 nm, about 300 nm to about 500 nm, about 300 nm to about 600 nm, about 300 nm to about 700 nm, about 400 nm to about 500 nm, about 400 nm to about 600 nm, about 400 nm to about 700 nm, about 500 nm to about 600 nm, about 500 nm to about 700 nm or about 600 nm to about 700 nm. The CP may emit fluorescence in the range of about 350 nm to about 700 nm.

The CP may have a charge. The charge may make the CPs soluble in water. The CP may be a conjugated polyelectrolyte (CPE). The CPE may be amphiphilic. The CPE may comprise a hydrophobic backbone, hydrophilic side groups or any mixtures thereof. The CPE may be anionic or cationic. The CPE may comprise ionizable side groups. The ionizable side groups may be anionic or cationic. The CPE may be anionic or cationic. The ionizable side groups may be selected from the group consisting of any one of carboxylate, primary ammonium, secondary ammonium, tertiary ammonium, histidinium, primary imide, secondary imide, sulfide, sulfonate, sulfonamide, phosphate, phenol and any mixtures thereof.

The ionizable side groups may be selected from the group consisting of salts of any one of carboxylate, primary ammonium, secondary ammonium, tertiary ammonium, histidinium, primary imide, secondary imide, sulfide, sulfonate, sulfonamide, phosphate, phenol and any mixtures thereof. The anionic CPE may be a polymer of;

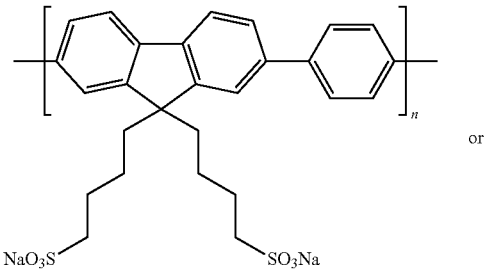

or

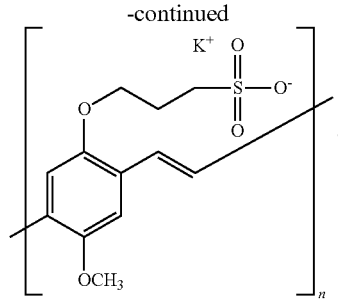

The cationic CP may be a polymer of;

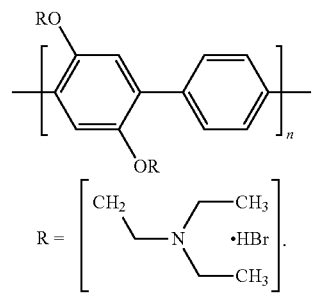

CPEs may be water-soluble by virtue of their charges, making them suitable for use in bioassays where the solvent is an aqueous solution. The CPE may couple optoelectronic/redox properties of the conjugated backbone with solubility in polar solvents and processability due to the ionic solubilizing groups. More advantageously, CPEs may be amphiphilic due to their hydrophobic backbone and hydrophilic side group, making them useful for simultaneously interacting with proteins, nucleic acids, NPs or any mixture thereof.

The "n" value may be in the range of any one of about 3 to about 100, about 3 to about 10, about 3 to about 50, about 10 to about 50, about 10 to about 100 or about 50 to about 100. The larger the "n" value, the more positive or more negative the charge of the CP may be, and this may increase the sensing ability of the sensor.

The fluorescence of the CP may be enhanceable or quenchable.

The fluorescence of the CP may be enhanceable. The enhancement may be dependent on the interaction between a fluorescence donor and a fluorescence acceptor. The enhancement may be dependent on any one of the distance between a fluorescence donor and a fluorescence acceptor, the overlap of the emission spectrum of the fluorescence donor and the absorbance spectrum of the fluorescence acceptor, the relative orientation between the fluorescence donor and the fluorescence acceptor or any mixture thereof. The sensor may be enhanceable by metal enhanced fluorescence (MEF).

The fluorescence donor may be the CP. The fluorescence acceptor may be the NP onto which the double stranded nucleic acid molecule is bonded. The NP onto which the double stranded nucleic acid molecule is bonded may enhance the fluorescence of the fluorescent CP. The NP may have a broad absorbance spectrum and high extinction coefficient, which may facilitate the use of a variety of CPs with a range of different emission spectra. An NP that has a diameter in the range of about 80 nm to about 200 nm may facilitate fluorescence enhancement of CPs. When a CP is brought into contact with an NP onto which the double stranded nucleic acid molecule is bonded, and the NP has a diameter in the range of about 80 nm to about 200 nm, the fluorescence of the CP may be enhanced.

The fluorescence of the fluorescent CP may be quenchable. The quenching may be dependent on the interaction between a fluorescence donor and a fluorescence acceptor. The quenching may be dependent on any one of the distance between a fluorescence donor and a fluorescence acceptor, the overlap of the emission spectrum of the fluorescence donor and the absorbance spectrum of the fluorescence acceptor, the relative orientation between the fluorescence donor and the fluorescence acceptor or any mixture thereof. The sensor may be quenchable by static quenching or dynamic quenching. The sensor may be quenchable by any one of Foerster Resonance Energy Transfer (FRET), Dexter electron transfer, nanoparticle surface energy transfer (NSET) or any mixture thereof.

The fluorescence donor may be the CP. The fluorescence acceptor may be the NP onto which the double stranded nucleic acid molecule is bonded. The NP onto which the double stranded nucleic acid molecule is bonded may quench the fluorescence of the fluorescent CP. The NP may have a broad absorbance spectrum and high extinction coefficient, which may facilitate the use of a variety of CPs with a range of different emission spectra. An NP that has a diameter in the range of about 10 nm to about 70 nm may facilitate fluorescence quenching of CPs. When a CP is brought into contact with an NP onto which the double stranded nucleic acid molecule is bonded, and the NP has a diameter in the range of about 10 nm to about 70 nm, the fluorescence of the CP may be quenched.

The fluorescence of the CP may be quenched by any one of about 10% to about 90%. The fluorescence of the anionic CP may be quenched by about 10% to about 60%, about 10% to about 20%, about 10% to about 30%, about 10% to about 40%, about 10% to about 50%, about 20% to about 30%, about 20% to about 40%, about 20% to about 50%, about 20% to about 60%, about 30% to about 40%, about 30% to about 50%, about 30% to about 60%, about 40% to about 50%, about 40% to about 60% or about 50% to about 60%. The fluorescence of the anionic CP may be quenched by about 10% to about 50%.

The fluorescence of the cationic CP may be quenched by any one of about 60% to about 90%, about 60% to about 70%, about 60% to about 80%, about 70% to about 80%, about 70% to about 90% or about 80% to about 90%. The fluorescence of the cationic CP may be quenched by about 80% to 90%.

The quenching of the anionic CP may be less than the quenching of fluorescence for the cationic CP due to electrostatic interactions between the CP and the double stranded nucleic acid molecule bonded onto the NP. Since the double stranded nucleic acid is negatively charged, anionic CPs may experience electrostatic repulsion, therefore may not be able to come into sufficient proximity with the NP, decreasing the efficiency of quenching of fluorescence. In contrast, the quenching of fluorescence of the cationic CP may be higher due to electrostatic attraction between the negatively charged double stranded nucleic acid molecules and the cationic CP, bringing the CP into closer proximity of the NP, facilitating increased quenching of fluorescence.

The fluorescence of the CP may be restored when brought into contact with a positively charged protein or a negatively charged protein. The fluorescence of the CP quenched in the presence of an NP that has a diameter in the range of about 10 nm to about 70 nm, may be restored when brought into contact with a positively charged protein or a negatively charged protein. The fluorescence of the CP quenched in the presence of an NP that has a diameter in the range of about 10 nm to about 70 nm, may be restored when a positively charged protein or a negatively charged protein binds to the nucleic acid molecule bonded onto the NP.

The quenched fluorescence of the anionic CP may be restored when a negatively charged protein binds to the nucleic acid molecule bonded onto the NP. The quenched fluorescence of the cationic CP may be restored when a negatively charged protein binds to the nucleic acid molecule bonded onto the NP. The quenched fluorescence of the anionic CP may be restored when a positively charged protein binds to the nucleic acid molecule bonded onto the NP. The quenched fluorescence of the cationic CP may be restored when a positively charged protein binds to the nucleic acid molecule bonded onto the NP.

The fluorescence of the CP may be further quenched when a positively charged protein or a negatively charged protein binds to the nucleic acid molecule bonded onto the NP. The fluorescence of the CP quenched in the presence of NP that has a diameter in the range of about 10 nm to about 70 nm, may be further quenched when a positively charged protein or a negatively charged protein binds to the nucleic acid molecule bonded onto the NP.

The quenched fluorescence of the anionic CP may be further quenched when a negatively charged protein binds to the nucleic acid molecule bonded onto the NP. The quenched fluorescence of the cationic CP may be further quenched when a negatively charged protein binds to the nucleic acid molecule bonded onto the NP. The quenched fluorescence of the anionic CP may be further quenched when a positively charged protein binds to the nucleic acid molecule bonded onto the NP. The quenched fluorescence of the cationic CP may be further quenched when a positively charged protein binds to the nucleic acid molecule bonded onto the NP.

An appropriate combination of CPs and NP, to allow an intermediate initial fluorescence quenching of the CP prior to protein detection, may be desirable since it may facilitate dual-sensing of both positive and negative proteins.

The fluorescence of the CP may be quenched when brought into contact with a positively charged protein or a negatively charged protein. The fluorescence of the CP enhanced in the presence of an NP that has a diameter in the range of about 80 nm to about 200 nm may be quenched when a positively charged protein or a negatively charged protein binds to the nucleic acid molecule bonded onto the NP. The fluorescence of the CP enhanced in the presence of NP that has a diameter in the range of about 80 nm to about 200 nm, may be quenched when a positively charged protein or a negatively charged protein binds to the nucleic acid molecule bonded onto the NP.

The enhanced fluorescence of the anionic CP may be quenched when a negatively charged protein binds to the nucleic acid molecule bonded onto the NP. The enhanced fluorescence of the cationic CP may be quenched when a negatively charged protein binds to the nucleic acid molecule bonded onto the NP. The enhanced fluorescence of the anionic CP may be quenched when a positively charged protein binds to the nucleic acid molecule bonded onto the NP. The enhanced fluorescence of the cationic CP may be quenched when a positively charged protein binds to the nucleic acid molecule bonded onto the NP.

The fluorescence of the CP may be further enhanced when a positively charged protein or a negatively charged protein binds to the nucleic acid molecule bonded onto the NP. The fluorescence of the CP enhanced in the presence of an NP that has a diameter in the range of about 80 nm to about 200 nm, may be further enhanced when a positively charged protein or a negatively charged protein binds to the nucleic acid molecule bonded onto the NP.

The enhanced fluorescence of the anionic CP may be further enhanced when a negatively charged protein binds to the nucleic acid molecule bonded onto the NP. The enhanced fluorescence of the cationic CP may be further enhanced when a negatively charged protein binds to the nucleic acid molecule bonded onto the NP. The enhanced fluorescence of the anionic CP may be further enhanced when a positively charged protein binds to the nucleic acid molecule bonded onto the NP. The enhanced fluorescence of the cationic CP may be further enhanced when a positively charged protein binds to the nucleic acid molecule bonded onto the NP.

A use for the sensor comprising: (a) noble metal nanoparticle (NP); (b) a first single stranded nucleic acid molecule bonded onto the NP; (c) a second, single stranded nucleic acid molecule, which is partially or completely complementary to the first nucleic acid molecule and is hybridized to the first nucleic acid molecule, to form a double stranded nucleic acid molecule capable of binding with a protein in an aqueous solution; and (d) an enhanceable or quenchable fluorescent conjugated polymer (CP) may be for sensing nucleic acid-protein interactions.

The sensor comprising: (a) noble metal nanoparticle (NP); (b) a first single stranded nucleic acid molecule bonded onto the NP; (c) a second, single stranded nucleic acid molecule, which is partially or completely complementary to the first nucleic acid molecule and is hybridized to the first nucleic acid molecule, to form a double stranded nucleic acid molecule capable of binding with a protein in an aqueous solution; and (d) an enhanceable or quenchable fluorescent conjugated polymer (CP) may be used in an assay kit for sensing nucleic acid-protein interactions.

A method for sensing nucleic acid-protein interactions may comprise the steps of: (i) bringing an aqueous solution suspected to comprise or known to comprise a protein of interest with the sensor as defined above; and (ii) detecting the presence or absence of a fluorescent signal to determine the nucleic acid-protein binding.

Step (i) may further comprise a step of contacting the protein with a double stranded nucleic acid molecule bonded onto a NP.

The step of contacting the protein with a double stranded nucleic acid molecule bonded onto a NP may be performed at a nucleic acid:protein mole ratio in the range of any one of about 100:1 to about 1:100, about 100:1 to about 50:1, about 100:1 to about 1:1, about 100:1 to about 50:1, about 50:1 to about 1:1, about 50:1 to about 1:50, about 50:1 to about 1:100, about 1:1 to about 1:50, about 1:1 to about 1:100 or about 1:50 to about 1:100. The step of contacting the protein with a double stranded nucleic acid molecule bonded onto a NP may be performed at a nucleic acid:protein mole ratio in the range of about 50:1 to about 1:50.

The step of contacting the protein with a double stranded nucleic acid molecule bonded onto a NP may be performed for a duration in the range of any one of about 10 minutes to about 60 minutes, about 10 minutes to about 20 minutes, about 10 minutes to about 30 minutes, about 10 minutes to about 40 minutes, about 10 minutes to about 50 minutes, about 20 minutes to about 30 minutes, about 20 minutes to about 40 minutes, about 20 minutes to about 50 minutes, about 20 minutes to about 60 minutes, about 30 minutes to about 40 minutes, about 30 minutes to about 50 minutes, about 30 minutes to about 60 minutes, about 40 minutes to about 50 minutes, about 40 minutes to about 60 minutes or about 50 minutes to about 60 minutes. The step of contacting the protein with a double stranded nucleic acid molecule bonded onto a NP may be performed for a duration in the range of about 20 minutes to about 40 minutes Step (i) may further comprise a step of contacting a CP with the protein-bound double stranded nucleic acid molecule bonded onto a NP.

The step of contacting a CP with the protein-bound double stranded nucleic acid molecule bonded onto a NP may be performed at a CP:nucleic acid mole ratio in the range of any one of about 5:1 to about 1:5, about 5:1 to about 2:1, about 5:1 to about 1:1, about 5:1 to about 1:2, about 5:1 to about 1:5, about 2:1 to about 1:1, about 2:1 to about 1:2, about 2:1 to about 1:5, about 1:1 to about 1:2, about 1:1 to about 1:5 or about 1:2 to about 1:5. The step of contacting a CP with the protein-bound double stranded nucleic acid molecule bonded onto a NP may be performed at a CP:nucleic acid mole ratio in the range of about 2:1 to about 1:1.

The step of contacting a CP with the protein-bound double stranded nucleic acid molecule bonded onto a NP may be performed for a duration in the range of any one of about 3 minutes to about 20 minutes, about 3 minutes to about 8 minutes, about 3 minutes to about 12 minutes, about 2 minutes to about 15 minutes, about 8 minutes to about 12 minutes, about 8 minutes to about 15 minutes, about 8 minutes to about 20 minutes, about 12 minutes to about 15 minutes, about 12 minutes to about 20 minutes or about 15 minutes to about 20 minutes. The step of contacting a CP with the protein-bound double stranded nucleic acid molecule bonded onto a NP may be performed for a duration in the range of about 8 minutes to about 12 minutes.

A method for sensing nucleic acid-protein interactions may further comprise a step of contacting the protein with ligand prior to contacting the protein with the double stranded nucleic acid molecule bonded onto a NP. The ligand may refer to small molecules that may bind to proteins. The ligand may be a positive ligand or a negative ligand. A positive ligand may refer to a ligand that may inhibit protein binding to nucleic acid, while a negative ligand may be a ligand that does not inhibit the binding. A ligand may bind strongly (with high affinity) to a certain protein but not inhibit the subsequent protein binding to nucleic acid and vice versa. The ligand may bind to the nucleic-acid binding domain motif of a protein. The ligand may not bind to the nucleic-acid binding domain motif of a protein but still modulate the nucleic acid-protein interaction.

The ligand may be a positive ligand. The ligand may inhibit nucleic acid-protein interaction. The positive ligand may be quinobene or Dawson. The positive ligand may inhibit the interaction between FoxA1 and its corresponding transcription factor recognition sequence, 5'-GTACTGTAAATAAAACT-3' (SEQ ID NO:3) hybridized to 5'-AGTTTTATTTACAGTAC-3' (SEQ ID NO:4).

The ligand may be a negative ligand. The ligand may not inhibit protein-nucleic interaction. The negative ligand may be any one of [[(Z)-(3-oxopyridin-2-ylidene)methyl]amino]thiourea (picolinaldehyde), 8-amino-10-phenylphenazin-2-one, 2-bromo-1H-phenalen-1-one, Lomofungin, N,N-dimethyldaunorubicin, 6H-Imidazo[4,1-de]acridin-6-one or Quinacrine. The negative ligand may not inhibit the interaction between FoxA1 and its corresponding transcription factor recognition sequence, 5'-GTACTGTAAATAAAACT-3' (SEQ ID NO:3) hybridized to 5'-AGTTTTATTTACAGTAC-3' (SEQ ID NO:4). The step of contacting the protein with ligand prior to contacting the protein with the double stranded nucleic acid molecule bonded onto a NP may be performed at a protein:ligand mole ratio of in the range of any one of about 1:2 to about 1:15, about 1:2 to about 1:5, about 1:2 to about 1:10, about 1:5 to about 1:10, about 1:5 to about 1:15 or about 1:10 to about 1:15. The step of contacting the protein with ligand prior to contacting the protein with the double stranded nucleic acid molecule bonded onto a NP may be performed at a protein:ligand mole ratio of in the range of about 1:5 to about 1:10.

The method for sensing nucleic acid-protein interactions may further comprise the step of calculating the binding constant $K_d$ of the nucleic acid-protein interaction using the following equation:

$$(F_0-F)/(F-F_{sat})=([protein]/K_d)^n,$$

wherein; [protein] is the concentration of the protein; F is the relative fluorescence intensity in the presence of protein; $F_0$ is the relative fluorescence intensity in the absence of protein; $F_{sat}$ is the relative fluorescence intensity in protein saturation; and n is the binding stoichiometry of protein to nucleic acid.

The method for sensing nucleic acid-protein interactions may be used for any one of determining the presence of nucleic acid-protein interaction, quantifying the $K_d$ of the nucleic acid-protein interaction, quantifying the stoichiometric ratio of the nucleic acid-protein ratio, determining the protein quality (denaturation or proper folding), determining inhibitors of nucleic acid-protein interaction, or detecting the impact of single nucleotide mutation on nucleic acid-protein interaction or for drug screening.

A method for sensing nucleic acid-protein interactions may comprise the steps of: (i) bringing an aqueous solution suspected to comprise or known to comprise a protein of interest with a sensor comprising;
 a. a noble metal nanoparticle (NP);
 b. a single stranded nucleic acid molecule capable of binding with a protein in an aqueous solution bonded onto the NP; and
 c. an enhanceable or quenchable fluorescent conjugated polymer (CP); and
(ii) detecting the presence or absence of a fluorescent signal to determine the nucleic acid-protein binding.

The method for sensing nucleic acid-protein interactions may facilitate sensing of nucleic-acid protein interactions that occur between a single stranded nucleic acid molecule and a protein that binds to a single stranded nucleic acid molecule.

The method for sensing nucleic acid-protein interactions may be used in an assay kit.

An assay for sensing nucleic acid-protein interactions may comprise the steps of: (i) bringing an aqueous solution suspected to comprise or known to comprise a protein of interest with the sensor as defined above; and (ii) detecting the presence or absence of a fluorescent signal to determine the nucleic acid-protein binding.

The assay for sensing nucleic acid-protein interactions may further comprise a step of contacting the protein with ligand prior to contacting the protein with the double stranded nucleic acid molecule bonded onto a NP.

The assay for sensing nucleic acid-protein interactions may further comprise the step of calculating the binding constant $K_d$ of the nucleic acid-protein interaction using the following equation:

$$(F_0-F)/(F-F_{sat})=([protein]/K_d)^n,$$

wherein; [protein] is the concentration of the protein; F is the relative fluorescence intensity in the presence of protein; $F_0$ is the relative fluorescence intensity in the absence of protein; $F_{sat}$ is the relative fluorescence intensity in protein saturation; and n is the binding stoichiometry of protein to nucleic acid.

The assay for sensing nucleic acid-protein interactions may be used for any one of determining the presence of nucleic acid-protein interaction, quantifying the $K_d$ of the nucleic acid-protein interaction, quantifying the stoichiometric ratio of the nucleic acid-protein ratio, determining the protein quality (denaturation or proper folding), determining inhibitors of nucleic acid-protein interaction, or detecting the impact of single nucleotide mutation on nucleic acid-protein interaction or for drug screening.

The disclosed sensor and method may have applications in screening a wide variety of nucleic acid-protein interactions, determining the presence or absence of nucleic acid-protein interactions, determining the $K_d$ of the nucleic acid-protein interaction, determining the stoichiometric ratio of the nucleic acid-protein ratio, the discovery of new therapeutic drugs, identification and characterization of small organic molecules that inhibit or weaken protein binding to DNA and studying protein quality (folding and denaturation) in their ability to bind nucleic acid molecules.

BRIEF DESCRIPTION OF DRAWINGS

The accompanying drawings illustrate disclosed embodiments and serve to explain the principles of the disclosed embodiments. It is to be understood, however, that the drawings are designed for purposes of illustration only, and not as a definition of the limits of the invention.

DETAILED DESCRIPTION OF DRAWINGS

Figure 1:
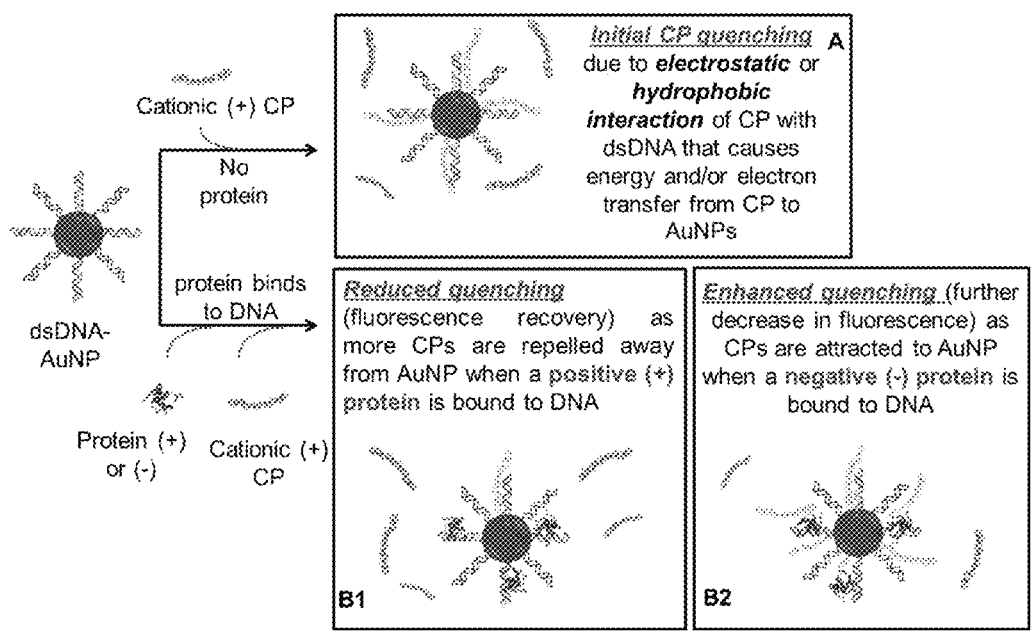
FIG. 1 is a schematic illustration of the assay concept using a cationic CP as an example.

FIG. 1 shows a schematic illustration of the assay concept with both fluorescent recovery (reduced quenching, B1) and fluorescent decrease (further quenching, B2) models with a cationic (+) CP as an example. (A) shows the initial fluorescence quenching without adding a protein. Binding of a positive protein will repel the CP and reduce the quenching (B1). Binding of a negative protein will enhance the quenching due to increased electrostatic attraction (B2).

EXAMPLES

Non-limiting examples of the invention will be further described in greater detail by reference to specific Examples, which should not be construed as in any way limiting the scope of the invention. Based on the foregoing disclosure, it should be clear that by the method, the objectives set forth herein can be fulfilled.

Example 1: Materials and Methods

DNA Sequences

Oligonucleotides (sense and antisense sequences, Table 1) were purchased from Sigma Life Science. For conjugation of the DNA, the sense sequences were thiol-labelled at the 5'-end for conjugation to AuNPs.

For FoxA1, three DNA probes of different affinity (named Probe1, Probe2, and Probe3, as described in Table 1), were studied. Probe2 is the ideal sequence for FoxA1 binding, containing the 5'-TAAAT-3' binding sequence (as indicated in bold in Table 1), while Probe1 and Probe3 are probes that have modifications in the sequence at the centre and flanking regions, respectively (as indicated with an underline in Table 1).

For AP-2γ, to demonstrate its affinity to GC-consensus, one GC rich DNA denoted as wild-type (wtR3) and one GC poor DNA called mutated-type (mtR3) were used (as described in Table 2). Similarly to the FoxA1 oligonucleotides in Table 1, the binding sequence is indicated in bold and the modifications in the mutated sequences are indicated with an underline in Table 2.

TABLE 1

DNA sequences for FoxA1

| DNA designation | Sequence |
| --- | --- |
| Probe1 | 5'-CACTTTGTTTGCAAAGC-3' (SEQ ID NO: 1) |
| Probe1-complementary | 5'-GCTTTGCAAACAAAGTG-3' (SEQ ID NO: 2) |
| Probe2 | 5'-GTACTGTAAATAAAACT-3' (SEQ ID NO: 3) |
| Probe2-complementary | 5'-AGTTTTATTTACAGTAC-3' (SEQ ID NO: 4) |
| Probe3 | 5'-<u>TGCCAAG</u>TAAAT<u>AGTGCAG</u>-3' (SEQ ID NO: 5) |
| Probe3-complementary | 5'-CTGCACTATTTACTTGGCA-3' (SEQ ID NO: 6) |

TABLE 2

DNA sequences for AP-2γ

| DNA designation | Sequence |
| --- | --- |
| wtR3 | 5'-AAAGTGCCCAGAGCCCATG-3' (SEQ ID NO: 7) |
| wtR3-complementary | 5'-CATGGGCTCTGGGCACTTT-3' (SEQ ID NO: 8) |
| mtR3 | 5'-AAAGT<u>ATT</u>CAGA<u>AT</u>CCATG-3 (SEQ ID NO: 9) |
| mtR3-complementary | 5'-CATGGATTCTGAATACTTT-3' (SEQ ID NO: 10) |

Gold-Nanoparticles (AuNP)

The AuNPs were synthesized via citrate reduction method, following procedures known to a person skilled in the art. $HAuCl_4.3H_2O$ (99.99%) and trisodium citrate dehydrate (99.9%) were obtained from Aldrich Pte Ltd. The resulting AuNPs were approximately 13 nm in diameter and in a concentration of 5.33 nM, calculated according to Beer's law, using the extinction coefficient of $2.467 \times 10^8$ $M^{-1}$ $cm^{-1}$ for 13 nm AuNPs.

Thiolated single stranded DNA (ssDNA) was activated with tris(2-carboxyethyl)phosphine) (TCEP, 10 molar excess) and stirred for 10 min. The final solution was centrifuged, with a Sigma-Aldrich microcon centrifugal filter device, YM-3 (NMWCO 3 kDa), to remove TCEP before conjugation to AuNPs. Conjugation of activated thiol DNA to AuNP was done as described by Zhang et al. (JACS 2012, 134, 7266-7299). Activated DNA was mixed with AuNP at a desired ratio (100:1) and incubated for 5 mins. Then, the pH of solution was lowered to 3 and the salt concentration was increased to 30 mM by adding HCl and NaCl respectively. After 20 min, NaOH was added to return the pH to neutral range. The ssDNA-AuNP conjugation was completed in about 30 min using this method. The ssDNA-AuNPs conjugates were then annealed with its complementary DNA at 90° C. for 5 min and allowed to cool to room temperature (RT). The amount of bound dsDNA was quantified using thiazole orange staining after removing the unbound DNA via centrifugation.

Figure 2:
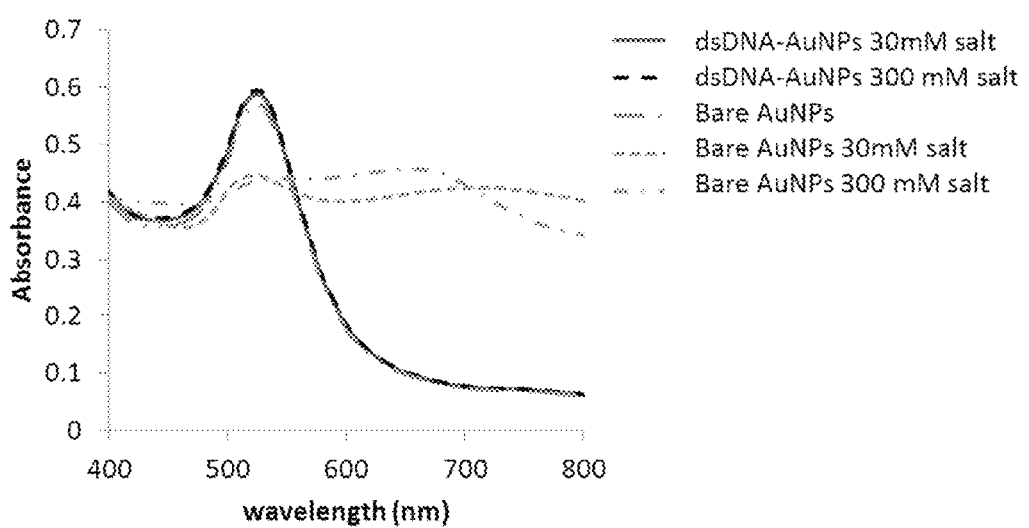
FIG. 2 is a graph showing the effect of salt concentration on the degree of agglomeration of dsDNA-AuNP and bare AuNP.

The dsDNA-AuNP entity can be kept in the fridge (4° C.) for several weeks without any precipitation since dsDNA provides a strong steric hindrance preventing the agglomeration of AuNPs. The completion of conjugation (or the successful DNA conjugation) was tested using salt (NaCl). As shown in FIG. 2, in the presence of NaCl (30 and 50 mM), aggressive aggregation was observed for the bare AuNP, indicated by the broadening of the absorbance peak. However, AuNPs protected with dsDNA can withstand higher salt concentration and remain well-dispersed in NaCl up to 300 mM (the highest concentration tested), as can be seen by the fact that the absorbance spectra of dsDNA-AuNP at 30 mM and 300 mM salt are almost overlapping.
Proteins Two transcription factors, FoxA1 and AP-2γ, were used as target proteins. Binding of FoxA1 and AP-2γ to DNA are sequence specific. Both FoxA1 and AP-2γ were kept as a 100 mM stock in 100 mM NaCl, 10 mM Tris-HCl, 2 mM TCEP. For long term storage, the proteins were kept as 10 mL aliquots at −80° C. Before use, they were quickly thawed in room temperature water bath and returned to 4° C. to maintain the activity.

FoxA1 was prepared as HisMBP-tagged FoxA1 recombinant protein. Full-length FoxA1 cDNA was cloned into a pHISMBP (Addgene) expression vector via the Gateway cloning system (Invitrogen) as described by the manufacturer. FoxA1 was expressed as a HisMBP fusion protein in BL21 (DE3) cells at 18° C. for 18 h of 0.5 mM IPTG induction in Terrific Broth (TB) media. Cells were collected by centrifugation, resuspended in a lysis buffer containing 50 mM Tris pH 8.0, 300 mM NaCl, 30 mM imidazole and sonicated on ice. Fusion proteins were initially purified from cell lysates using a nickel column equilibrated with the lysis buffer and eluted with the same buffer supplemented with 300 mM imidazole. A second purification step using ion exchange chromatography was performed by passing the sample through a Resource Q anion exchanger (GE Healthcare) and eluted in buffer containing 10 mM Tris-HCl, 1 M NaCl, pH 8.0, with a linear gradient from 0.1-1.0 M NaCl. Eluted fractions were collected, pooled, dialyzed against storage buffer (10 mM Tris-HCl, 100 mM NaCl, 2 mM TCEP, pH 8.0) and concentrated to approximately 100 mM using Vivaspin 20 concentrator before storing at −80° C. until use.

Protein purification of HisMBP-tagged AP-2γ protein was performed similarly to that for HisMBP-tagged FoxA1, except that after the nickel affinity purification step, the buffers used had a pH of 7.0. The HisMBP-AP-2γ protein was subsequently purified using the Hi-Trap Heparin HP column (GE healthcare) with A1 (10 mM HEPES, 100 mM NaCl; pH 7.0) and B1 (10 mM HEPES, 1 M NaCl; pH 7.0) buffers. Eluted fractions containing the fusion protein were pooled together, concentrated in a 30 kDa concentrator and desalted twice in A4 buffer. The protein was then stored at −80° C. in 100 mM aliquots.
Ligands 9 small ligands (as described in Table 3) were used to disrupt the DNA-protein interaction. A positive ligand refers to a ligand that can inhibit protein binding to DNA, while a negative ligand is a ligand that does not interrupt the binding. It must be clearly understood that a particular ligand can bind strongly (with high affinity) to a certain protein but not inhibit the subsequent protein binding to DNA and vice versa. The main objective of this assay is to screen ligands that can interrupt protein binding to DNA regardless of their affinity to the protein. All of the ligands were kept as solutions in DMSO. Before using, they were thawed in a room temperature water bath.

TABLE 3

Low molecular weight ligands from the diversity, mechanistic and natural products libraries procured from the National Cancer Institute.

| Ligand No. | Name | Selectivity for FoxA1 and AP2γ | MW |
|---|---|---|---|
| 1 | Quinobene | Positive (inhibitor) | 931 |
| 2 | Dawson | Positive (inhibitor) | 3015 |
| 3 | [[(Z)-(3-oxopyridin-2-ylidene)methyl]amino]thiourea (picolinaldehyde) | Negative | 196 |
| 4 | 8-amino-10-phenylphenazin-2-one | Negative | 287 |
| 5 | 2-bromo-1H-phenalen-1-one | Negative | 259 |
| 6 | Lomofungin | Negative | 314 |
| 7 | N,N-dimethyldaunorubicin | Negative | 556 |
| 8 | 6H-Imidazo[4,1-de]acridin-6-one | Negative | 415 |
| 9 | Quinacrine | Negative | 436 |

Conjugated Polymers (CPs)

Three conjugated polymers (CPs) were utilized for proof of concept, including 2 anionic (−) CPs (ACPs) and one cationic (+) CP (CCPs). The CPs were all water soluble. The ACPs were made of poly[9,9-bis(40-sulfonatobutyl)fluorene-co-alt-1,4-phenylene] sodium salt (PFP-SO3Na) and poly[5-methoxy-2-(3-sulfopropoxy)-1,4-phenylenevinylene] potassium salt. The CCP was made of poly[(2,5-bis(2-(N,N-diethylammoniumbromide)ethoxy)-1,4-phenylene)-alt-1,4-phenylene].

The two ACPs emit fluorescence at different wavelengths of 430 nm and 560 nm, respectively, and thus are denoted as ACP-430 and ACP-560, respectively. The cationic polymer emits fluorescence at 410 nm and thus is denoted as CCP-410. For all CPs, the number following the type of CP (anionic or cationic) denotes the wavelength corresponding to the emission peak. The chemical structures of the CPs are shown below. Both anionic and cationic CPs of different emitting wavelengths were used to elucidate the generality of the assay for proteins of different charges.

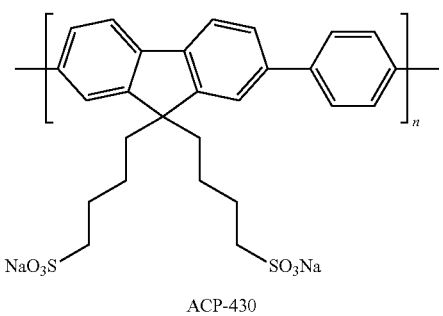

ACP-430

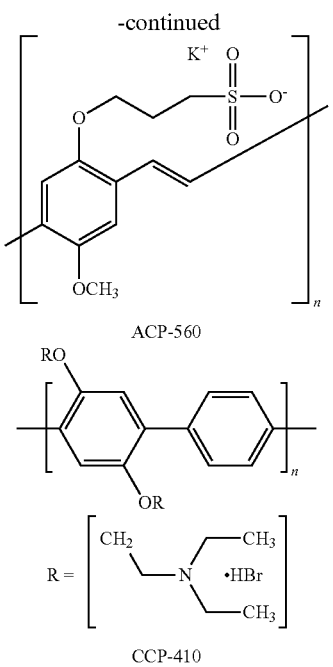

ACP-560

CCP-410

The ACP-560 and CCP-410 were purchased from Sigma Aldrich, while the ACP-430 was provided by Prof. Liu Bin (National University of Singapore). ACP-430 has been previously used for detecting lysozymes using organic dye-CPs and FRET.

Figure 3:
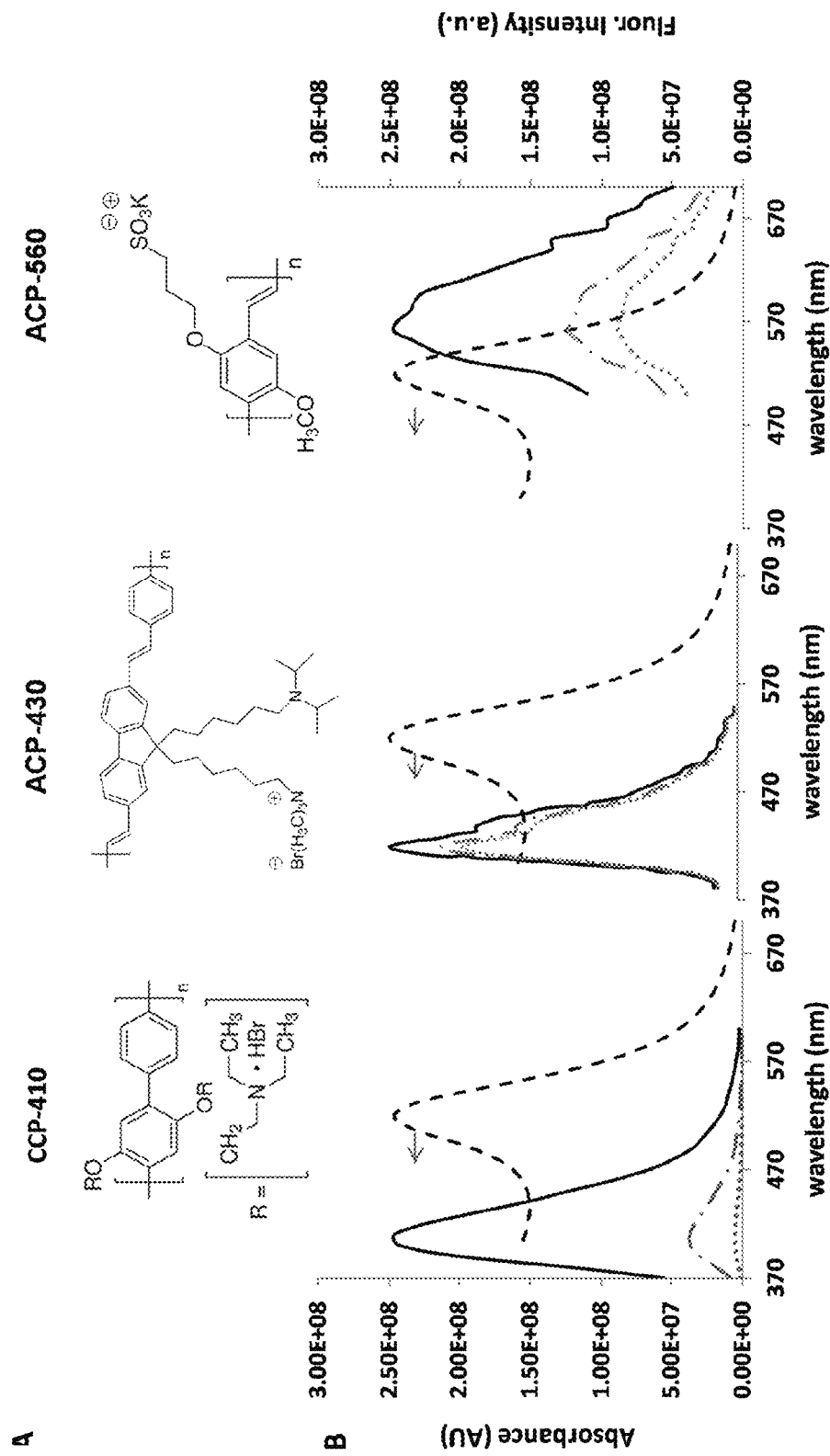
FIG. 3 is a graph showing the absorbance spectra of AuNPs (dashed lines), fluorescence emission spectra of the free CPs (solid lines), fluorescence emission spectra of the CPs following initial quenching by the dsDNA-AuNPs (dash-dot lines) and fluorescence emission spectra of the CPs following initial quenching by bare AuNPs (dotted lines).

The optical spectra of the three CPs and the absorbance spectra of dsDNA-AuNP used in the assay are shown in FIG. 3.

Measurement of Hydrodynamic Size and Zeta Potential

The hydrodynamic size and zeta potential of AuNPs before and after conjugation with dsDNA, as well as those after protein and CPs binding, were measured with a Dynamic Light Scattering System (BI-200SM, Brookhaven Instruments Corporation). The measurements were performed in water for AuNPs and dsDNA-AuNPs, and in 5 mM HEPES buffer for protein and CP-bound dsDNA-AuNPs.

Alternative Assays

Electrophoretic Mobility Shift Assay (EMSA): Invitrogen Corporation, Panomics Inc., Pierce Biotechnology, Viagene Inc.

Transcription Factor (TF) Enzyme-Linked Immunosorbent Assay (ELISA): Panomics Inc. and Pierce Biotechnology.

Fluorescence anisotropy (FA): To determine the binding activity of His-MBP-FoxA1 to various FoxA1 probes containing its cognate DNA element, fluorescence anisotropy (FA) assay was utilized. The wildtype and two mutant probes for FoxA1, labelled with carboxyfluorescein (FAM), are as described earlier in Table 1. The assays were carried out in 384-well microplates (Corning) in which varying concentrations of protein were incubated with 2 nM of the labelled probe in PBS buffer for 20 min at room temperature (RT). To examine the effects of small molecule inhibitors on FoxA1 DNA binding, 125 nM of protein was pre-incubated with 5% DMSO, or 1 mM unlabelled probe, or 1.9 mM inhibitor for 1 h, at room temperature (RT), before the addition of 2 nM of the FAM labelled probe for another hour incubation.

Fluorescence anisotropy was measured using Synergy 2 Multi-Mode Microplate Reader with a 485/20-excitation and a 528/20-emission filter. The equilibrium dissociation constants for each wild-type probe were subsequently calculated by fitting the FoxA1 concentration vs. fluorescence polarization plot using Langmuir isotherm in Origin Pro 8 software. Standard error values (precision of the fitted values) were also obtained from the software after fitting.

Example 2: Overview of Binding Assay

Figure 4A:
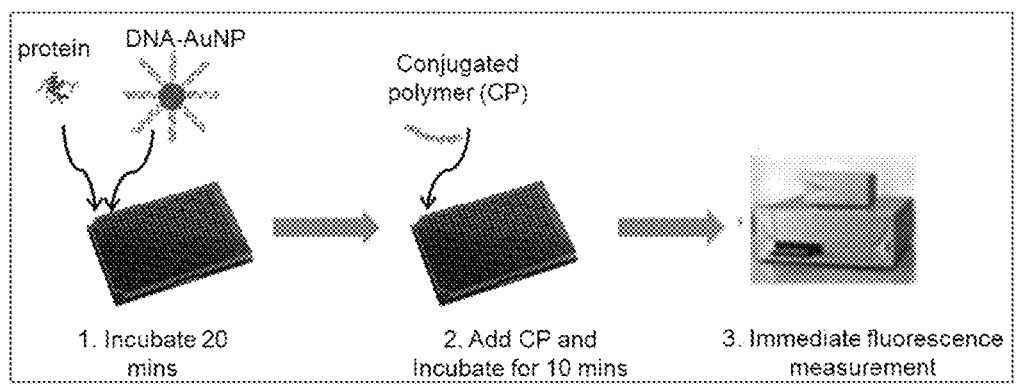
FIG. 4(A) is a schematic diagram showing the assay procedures for studying the DNA-protein interaction.

The protein-DNA binding assay was conducted in three main steps (FIG. 4(A)):
1) 50 nM dsDNA-AuNPs (referring to dsDNA concentration on the surface of AuNPs) was incubated with protein for 20-40 min at room temperature (RT). To determine the binding constant ($K_d$) and the stoichiometry, protein titration was conducted with increasing concentration of protein from 0-250 nM.
2) CP at a concentration of 100 nM (i.e. 2:1 molar ratio to dsDNA-AuNP) was added to the dsDNA-AuNPs-protein mixture and incubated for an additional 10 min to let the system reach equilibrium.
3) The fluorescence spectra of the final solution was measured and compared to a control without any protein. Depending on the charge of the protein and the CPs used, the protein-DNA binding was observed to lead to further fluorescence quenching or fluorescence recovery.

Figure 4B:
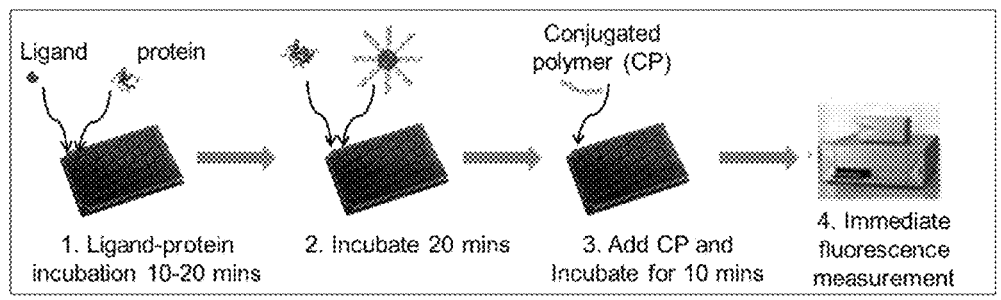
FIG. 4(B) is a schematic diagram showing the assay procedures for screening ligand inhibition of the DNA-protein interaction.

For screening of ligand inhibition of the DNA-protein interaction (FIG. 4(B)), the ligand and protein were incubated at a molar ratio of 8:1 for 10-20 min at RT prior to the addition of dsDNA-AuNP in step (1) above. Steps (1), (2) and (3) were then repeated.

Figure 5:
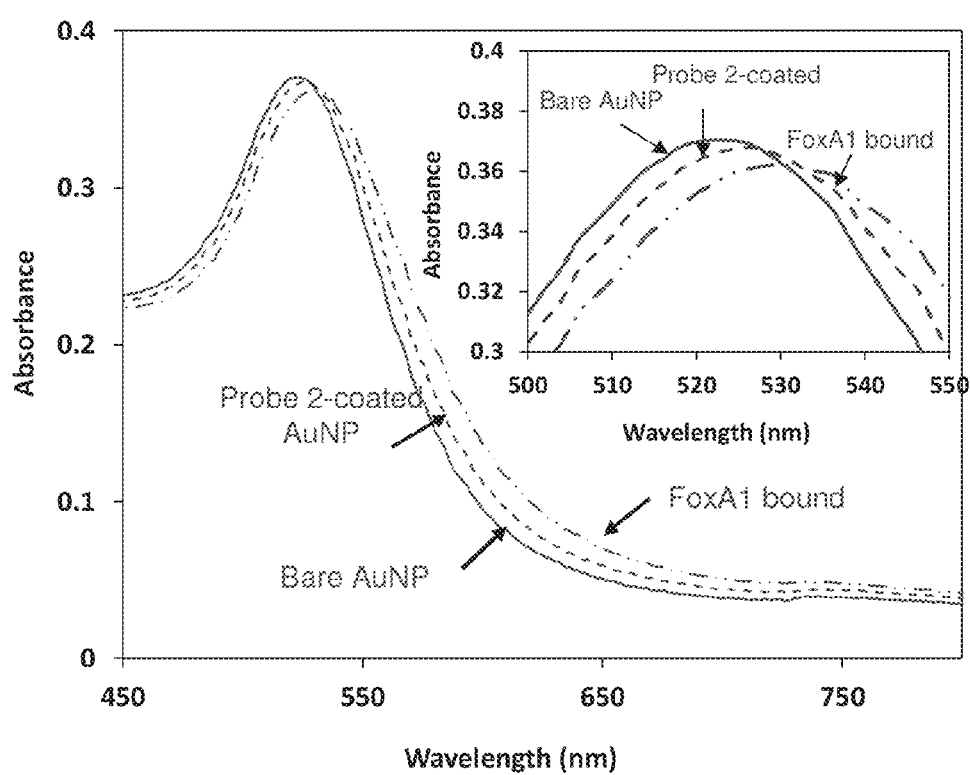
FIG. 5 is a graph showing the absorbance spectrum of AuNPs and AuNPs coated with 17-mer dsDNA (Probe2), before and after FoxA1 binding.

Example 3: Characterization of the Interactions Between dsDNA, AuNPs, Proteins, Ligands and CPs Double stranded DNA (dsDNA) conjugated AuNPs is one of the key sensing elements in this study (DNA sequences used on this study are described in Tables 1 and 2). As shown in FIG. 5, the successful binding of the DNA to AuNPs can be confirmed by the slight red shift of the peak wavelength of 4 nm. The surface charge and hydrodynamic size of the 13 nm AuNPs before and after DNA conjugation, as well as the surface coverage of the dsDNA on AuNPs are characterized and summarised in Table 4.

FIG. 5 also shows the absorbance spectrum of AuNPs and AuNPs conjugated with the 17-mer DNA (Probe2) before and after FoxA1 binding. Following addition of protein and/or ligand, the absorbance of dsDNA-AuNP did not show any change. Therefore, it was found that it was important for a reporter compound, in this case CP, to be added to the reaction to indicate the protein binding event to the DNA attached to the AuNP.

TABLE 4

Characteristics of AuNPs, dsDNA (17 bp FoxA1 probe)-conjugated AuNPs, protein (FoxA1) bound dsDNA-AuNPs and CP-bound protein-dsDNA-AuNPs.

| Particles | Hydrodynamic diameter (nm) | Zeta potential (mV) | DNA surface coverage (molar ratio) |
|---|---|---|---|
| Bare AuNP | 20.4 ± 2.18 | −39.2 ± 3.5 | N.A. |
| dsDNA-AuNP | 31.9 ± 0.91 | −32.7 ± 2.8 | 99.7 ± 6.0 |
| FoxA1 bound dsDNA-AuNP | 52.8 ± 1.7 | −25.8 ± 2.5 | |

TABLE 4-continued

Characteristics of AuNPs, dsDNA (17 bp FoxA1 probe)-
conjugated AuNPs, protein (FoxA1) bound dsDNA-
AuNPs and CP-bound protein-dsDNA-AuNPs.

| Particles | Hydrodynamic diameter (nm) | Zeta potential (mV) | DNA surface coverage (molar ratio) |
|---|---|---|---|
| ACP-430-bound FoxA1-dsDNA-AuNP | 53.4 ± 1.9 | −26.3 ± 2.3 | |
| CCP-410-bound FoxA1-dsDNA-AuNP | 53.8 ± 0.3 | −24.6 ± 5.7 | |

The hydrodynamic size expansion from 20.4±2.18 nm to 31.9±0.91 nm (i.e. an increase of 11.5 nm) confirmed that the by dsDNAs are fully extended like a rigid rod on the surface of the AuNPs, based on the fact that every 10 bp of a DNA double helix is approximately 3.4 nm in length (it should be noted that in this estimation the C6 thiol linker was not taken into consideration).

Based on the zeta potential measurements, the surface charge density is slightly reduced from −39.2±3.5 mV to −32.7±2.8 mV following DNA conjugation. However, this is still substantial enough to act as a molecular screen that wanes the negative charge. That is, the overall negative charge of the AuNP is still sufficiently high that the ds-DNA-AuNP will maintain its electronic properties. Taking into account the wavelength shift in the absorbance maximum, the expanded hydrodynamic size and the change in surface charge, the successful conjugation of the dsDNA onto the AuNP surface is confirmed.

To study the ability of dsDNA-AuNPs conjugates at quenching the CP fluorescence emission, the NPs and CPs were mixed at equal mole ratios; the CP fluorescence emission was measured and compared with the same concentration of CPs without NPs. FIG. 3 shows the emission spectra of the three CPs with and without addition of the 17 bp dsDNA-AuNPs (or bare AuNPs). The absorbance spectra of AuNPs (or dsDNA-AuNPs) is given as a reference to show the integral overlap of the CP (donor) emission and AuNP (acceptor) absorbance spectra that would dictate the initial quenching of CPs by dsDNA-AuNP.

All CPs showed a detectable decrease in fluorescence intensity due to the interaction between the CP with the dsDNA conjugated to the AuNPs. The dsDNA conjugated to the AuNP acts as a mediator for energy and/or electron transfer between the CP and AuNP that results in non-radiative decay of fluorescence. The dsDNA brings the CP into close proximity of the AuNP for energy and/or electron transfer and thus non-radiative decay occurs, resulting in quenching of fluorescence. The degree of quenching is largely determined by the charge of the polymer and the spectrum overlap with the absorbance spectrum of the AuNP.

For example, the fluorescence of ACP-430 ($\lambda_{em}$=430 nm) was slightly quenched (by ~15%) when mixed with dsDNA-AuNPs. The emission peak was slightly blue shifted from 430 nm to 420 nm. The slight increase in energy gap of this polymer could be due to the change in conformation upon interacting with dsDNA. Since both ACP-430 polymer chain and dsDNA possess net negative charges, electrostatic attraction is not expected to exist between them, and in fact, there should be significant repulsion. Therefore, minimal fluorescence quenching was expected. Thus the slight fluorescence quenching of ~15% is presumably due to the hydrophobic interaction between the non-polar carbon chains of the CP and the molecular backbone of hydrophobic DNA that prefers to maintain a distance from polar water molecules in solvent.

This speculation was confirmed by decreasing the polarity of the solvent by adding chloroform. As the chloroform content was increased (up to 40 vol %), the degree of fluorescence quenching diminished gradually, resulting in only a small amount of quenching. It is believed that in less polar organic solvents, CPs can minimize its free energy and increase the entropy by having more random configurations without having to interact with the dsDNA.

To confirm that a significant amount of energy or electron transfer did not take place in the absence of AuNP, CP was incubated separately with only free dsDNA (no AuNP) or protein (FoxA1). Neither dsDNA nor FoxA1 quenched the fluorescence of CP. The change in fluorescence was therefore only observed in the presence of AuNPs.

For the other negatively charged polymer, ACP-560 ($\lambda_{em}$=560 nm), the overlap integral with the AuNP absorbance ($\lambda_{em}$=520 nm) is more than that for ACP-430 ($\lambda_{em}$=430 nm). Despite the same weak interaction with dsDNA, this ACP-560 was quenched to a larger degree (~50%) than the ACP-430. This indicates that larger degree of overlap between the CP fluorescence emission and the absorbance of the AuNPs is essential for strong energy transfer and thus increased fluorescence quenching.

In comparison with the negatively charged ACPs, positively charged CCP-410 ($\lambda_{em}$=410 nm) had similar spectral overlap with the AuNP absorbance spectrum as that for ACP-430. However, a much stronger quenching (~85%) was observed. This may be attributed to the intrinsic positive charge of the polymer chain that may interact electrostatically with the dsDNA-AuNP.

A shift in the emission peak is not observed for ACP-560 or CCP-410. One possible explanation for this is that both these CPs have a higher hydrophobicity and thus less likely to change conformation upon interacting with dsDNA, unlike the ACP-430 which is more hydrophilic. The stronger hydrophilic characteristic of ACP-430 is supported by its higher solubility in water.

To understand the effect of the dsDNA coating on the CP quenching by AuNPs, the quenching behaviour of bare AuNPs and dsDNA-AuNPs (FIG. 3, dotted lines versus dash-dot lines) were compared. As expected, bare AuNPs quenched the CPs stronger than the dsDNA-AuNP conjugates. In particular, the ACP-430 and ACP-560 were quenched by roughly 20% and 65%, respectively, compared to the 15% and 50% quenching observed with dsDNA-AuNPs, respectively. Further, CCP-410 was almost completely quenched by the unmodified AuNPs. The enhanced quenching by bare AuNPs can be attributed to the fact that the CPs could come into even closer proximity of the bare AuNP surface by direct attachment, while the quenching of CPs by ds-DNA AuNPs is distance dependent due to the presence of the dsDNA. That is, the closer the CP is to the AuNP, the more efficient the quenching process. The dsDNA coating (~11.5 nm thick) on the AuNP surface may act as a spatial barrier that prevents CPs from directly attaching to the AuNP, therefore diminishing the quenching efficiency.

Example 4: Detecting FoxA1-DNA Interactions Using ACP-430

To demonstrate the concept of the assay, the transcription factor FoxA1 and its corresponding DNA sequences (Probe1, Probe2, and Probe3) were used. mtR3 was used as a control DNA, as it does not bind with FoxA1. FoxA1 only exhibits a weak interaction with the dsDNA-AuNPs, detected as a smaller degree of initial quenching (~15%). For fast screening of FoxA1 affinity with different DNAs, FoxA1 was mixed and incubated with dsDNA-AuNPs at any molar ratio for 20 min, but higher protein:dsDNA-AuNP ratios were chosen for better differentiation. Following this, ACP-430 was added and incubated for 10 min.

FoxA1 has an isoelectric point (pI) of about 8.9, so has a positive charge at pH 7.4. The binding of this protein to dsDNA-AuNPs has been confirmed by the remarkable increase hydrodynamic size and the reduced negative charge of the nanoparticles, as shown in Table 4. Due to the binding of the positively charged FoxA1, the fluorescence intensity of ACP-430 was further suppressed as shown for the Probe2-DNA in FIG. 6.

Figure 6:
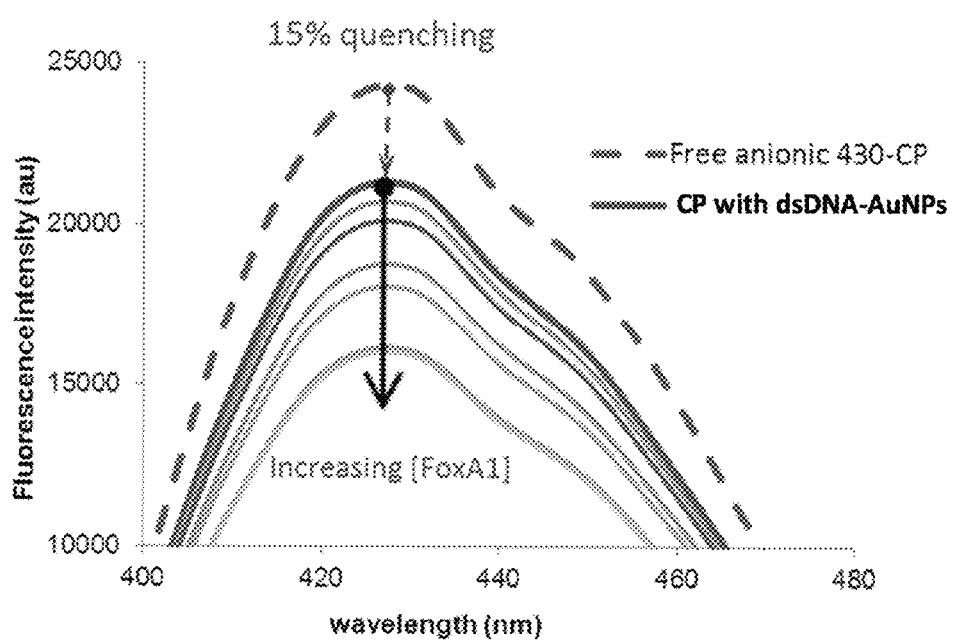
FIG. 6 is a graph showing the fluorescence emission spectra of free ACP-430 (dashed line) and ACP-430 incubated with Probe2-AuNP and FoxA1.

As FoxA1 binds to the DNA, it is expected to decrease the overall negative charge of the DNA. This will alter the magnitude of electrostatic interaction between DNA and the anionic CP. As the overall negative charge is lowered (becomes more positive), more anionic CPs could come in to closer proximity of the AuNP. As the distance becomes sufficiently close, increased energy or electron transfer from the CP to AuNP is thought to occur, whereby a non-radiative pathway causes excited electrons to decay to ground state, resulting in fluorescence quenching. Consequently, the measured fluorescence intensity of ACP-430 further decreases relative to that in the absence of protein (FIG. 6). That is, increased fluorescence quenching of the CP occurs in the presence of the protein.

Figure 7:
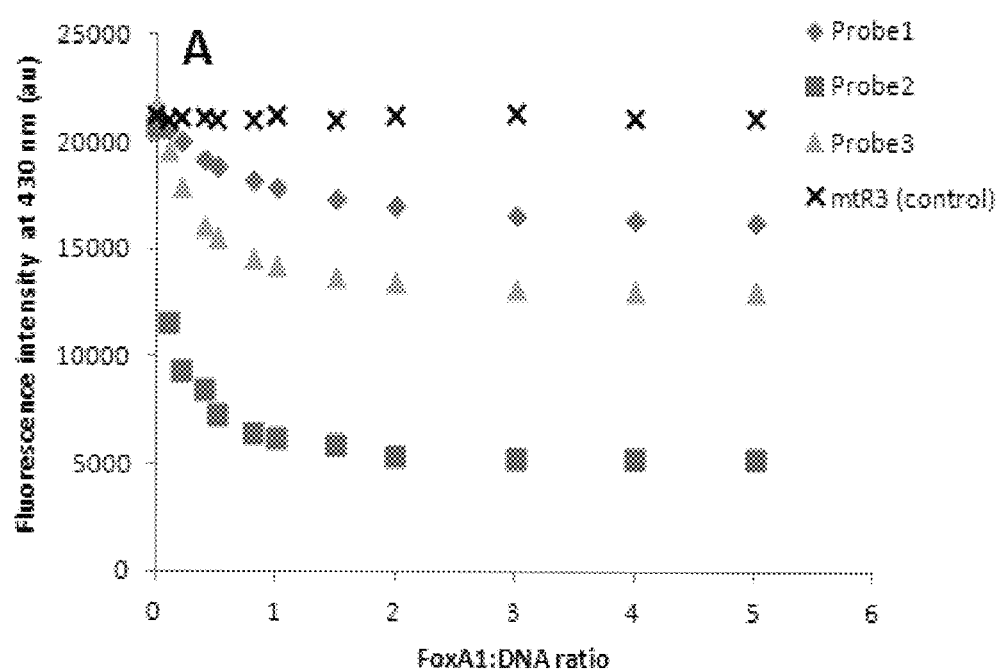
FIG. 7 is a graph showing the decrease in fluorescence intensity of ACP-430 as a function of FoxA1 concentration for Probe1, Probe2, and Probe3.

The fluorescence intensity decreased with increasing concentration of FoxA1 before reaching a saturation value for all three tested probes (FIG. 7). This may be due to the binding of FoxA1 to the DNA causing a neutralization of the negative charge of the dsDNA-AuNP to a certain degree, as shown by the zeta potential data in Table 4 (from −32.7±2.8 to −25.8±2.5 mV), and thus allowing more of ACP-430 to access the AuNP due to reduced charge repulsion. The increase of the negative charge density of FoxA1-bound dsDNA-AuNPs from 25.8±2.5 to −26.3±2.3 in the presence of ACP-430 further supports the binding of the negatively charged ACP-430 chains onto the FoxA1-bound dsDNA-AuNPs (Table 4).

When Probe1 and Probe3 were tested, the probes responded differently to Probe2 in the presence of protein and dsDNA-AuNP. As shown in FIG. 7, the protein concentration dependent fluorescence intensity decreased as a function of FoxA1 concentration for all probes tested, which indicated the formation of an increasing amount of the complex. The decrease in fluorescence intensity, or quenching strength, at a given protein concentration increased in the order of Probe2>Probe3>Probe1, which followed the affinity order of Probe2>Probe3>Probe1 for FoxA1. That is, the largest amount of fluorescence quenching was observed for AuNPs conjugated with Probe2, as Probe2 has the highest affinity for the FoxA1 protein hence bound the most number of proteins, causing the highest decrease in overall negative charge, allowing more CPs to come into closer proximity of the AuNPs such that increased energy or electron transfer and consequently quenching of fluorescence to occur. This trend was observed for any concentration of protein added, though the differentiation became more vivid at higher concentration. A negative control was also measured, which was mixture of mtR3-AuNP and FoxA1. The fluorescent intensity did not change with addition of FoxA1.

Example 5: Detecting FoxA1-DNA Interactions Using ACP-560

ACP-560 was also quenched by dsDNA-AuNP but to a higher extent (~50%) compared to ACP-430 (~15%), in the absence of protein. Although both the anionic CPs may interact with DNA via hydrophobic interactions, the large integral overlap between emission spectrum of the ACP-560 and the absorbance spectrum of AuNP results in a stronger quenching of ACP-560 in the presence of AuNP. The intermediate fluorescence quenching gives the ACP-560 its unique dual-application, where it could be used to detect protein binding either by fluorescence quenching or recovery, which is largely controlled by the charge of the protein of interest. If the protein is positively charged, binding of the protein will bring more ACP-560 to close proximity of the AuNP, which in turn will cause more fluorescence quenching. If the protein is negatively charged, it will repel more anionic CPs away, causing the fluorescence of the CP to recover (decreased quenching). This intermediate initial quenching is suitable for studying proteins of unknown charge.

Figure 8:
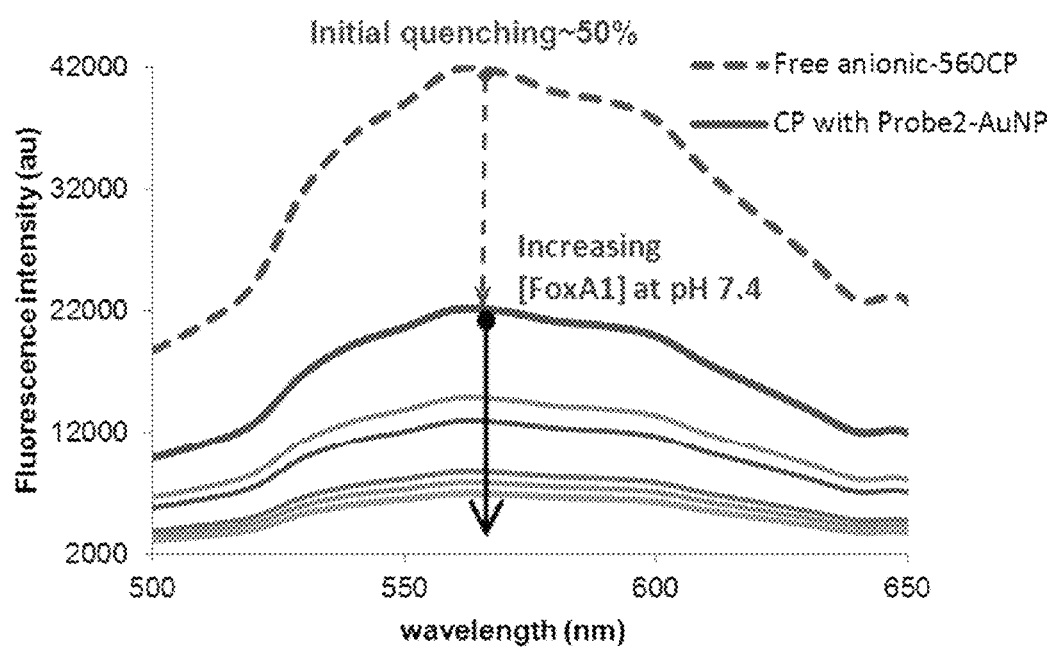
FIG. 8 is a graph showing the fluorescence emission spectra of free ACP-560 (dashed line) and ACP-560 incubated with Probe2-AuNP and FoxA1.
Figure 9A:
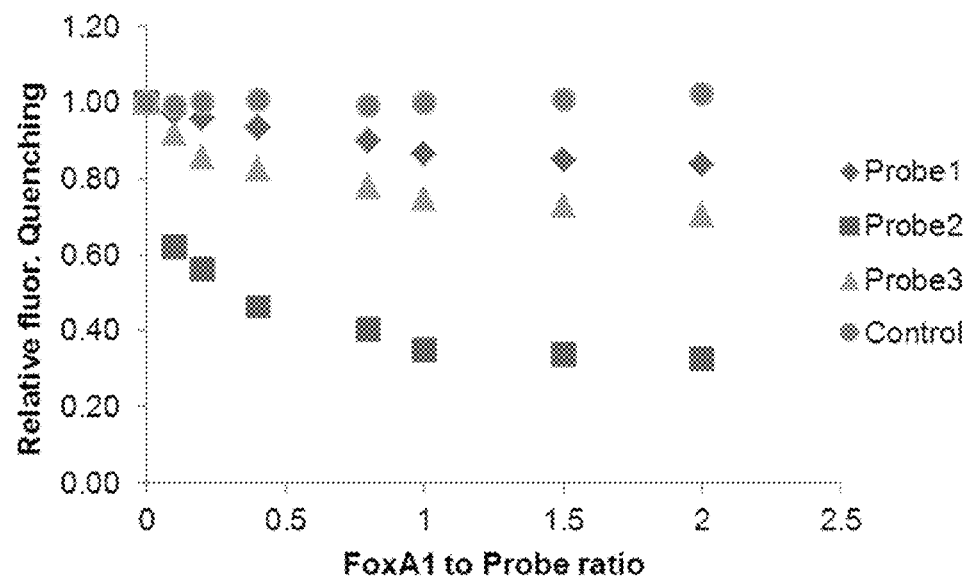
FIG. 9(A) is a graph showing the ACP-560 fluorescence titration of Probe1-, Probe2-, Probe3- and control (mtR3)-AuNP with FoxA1 at pH 7.4.
Figure 9B:
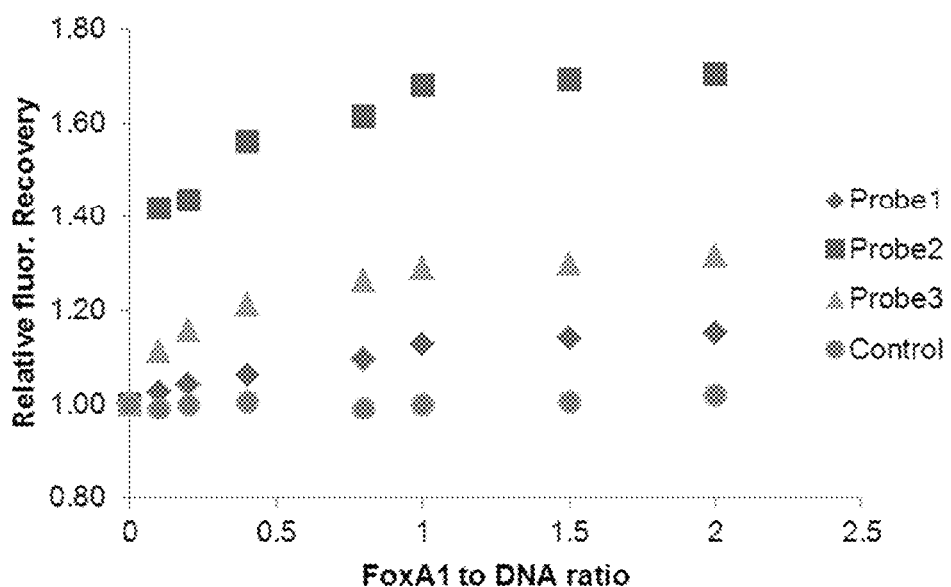
FIG. 9(B) is a graph showing the ACP-560 fluorescence titration of Probe1-, Probe2-, Probe3- and control (mtR3)-AuNP with FoxA1 at pH 9.5.

To show the dual-purpose of this CP for studying unknown proteins, both positive and negative charged proteins were tested. FoxA1 has a positive charge at pH 7.4, thus the fluorescence of the ACP-560, as shown in FIG. 8, is further quenched when FoxA1 binds to DNA. In order to generalize the concept, negatively charged FoxA1 was acquired by increasing the pH to 9.5 and its binding to AuNPs conjugated with Probe1, Probe2 or Probe2 (Probe1-, Probe2-, and Probe3-AuNPs, respectively) were tested using the same negatively charged ACP-560. FIGS. 9(A) and 9(B) show the response of ACP-560 as a function of FoxA1 concentration at pH 7.4 (positive FoxA1) and pH 9.5 (negative FoxA1). As the negatively charged FoxA1 bound to DNA, a net increase in negative charge occurs, causing a repulsion of ACP-560 further away from the surface of the AuNP, resulting in fluorescence recovery. The magnitude of change in intensity decreased in the order of Probe2>Probe3>Probe1, following the trend of ACP-430 in Example 4.

This method of detecting DNA-protein interaction would be particularly suitable for studying a protein when the isoelectric point is not known, especially as studying of proteins with unknown isoelectric points are often not possible by other FRET sensors involving CPs and an organic dye donor-acceptor pair.

Example 6: Detecting FoxA1-DNA Interactions Using CCP-410

Figure 10:
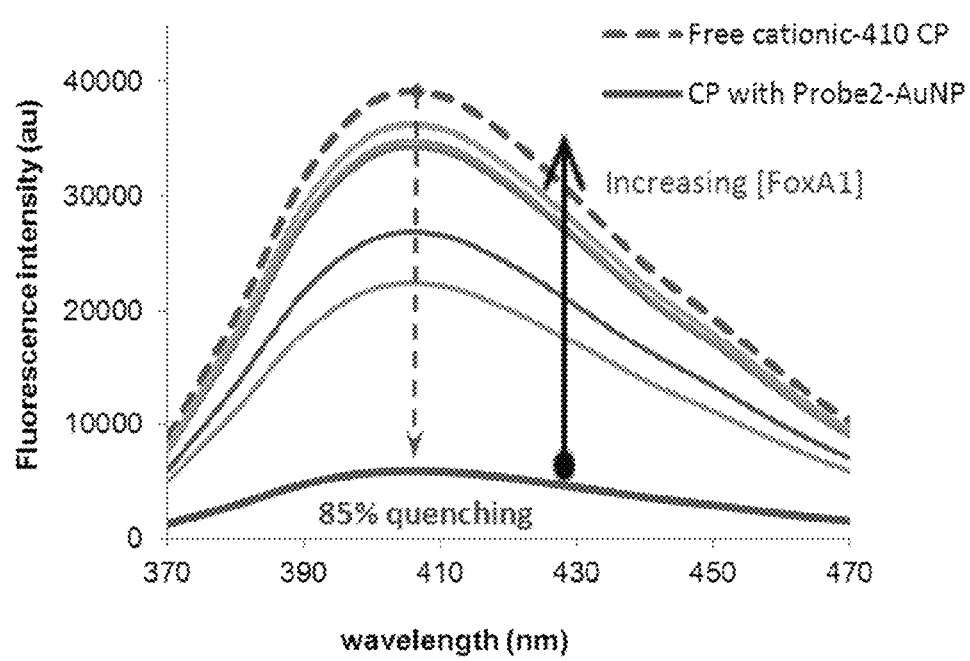
FIG. 10 is a graph showing the fluorescence emission spectra of free CCP-410 (dashed line) and CCP-410 incubated with Probe2-AuNP and FoxA1.

The third type of CP, CCP-410, has the opposite charge to ACP-430 but emits fluorescence at a similar wavelength. CCP-410 and ACP-430 exhibit almost similar degrees of spectral overlap with the AuNP absorbance spectra. However, CCP-410 was quenched more strongly (about 85%) by AuNP than ACP-430 when no protein was present, as shown in FIG. 10. This result clearly suggests that due to the opposite charges, there is a stronger electrostatic attraction between the DNA and CCP-410 that brings the CP closer to AuNP more efficiently. Increased binding of FoxA1 repels more cationic CP away from the surface of AuNP, thus fluorescence is restored or recovered upon protein binding, as shown in FIG. 10.

It is thought that when the FoxA1 which is positively charged at pH 7.4, binds to the DNA, the overall negative charge of the dsDNA-AuNP complex is neutralized, weakening the electrostatic binding between the positively charged CP and the dsDNA-AuNP. This is detected as reduced fluorescence quenching, or fluorescence restoration. At the highest FoxA1 concentration, the CCP-410 binding is minimal as shown by almost completely depleted quenching in FIG. 10 and the insignificant change of the zeta potential of the FoxA1-bound AuNP in Table 4. For the 3 DNA probes tested for FoxA1, the extent of fluorescence recovery followed the same order as that for ACP-430 in Example 4, where it was Probe2>Probe3>Probe1. A similar control experiment was conducted using a negative control DNA (mtR3-AuNP) which did not show appreciable change in fluorescence intensity.

Figure 11:
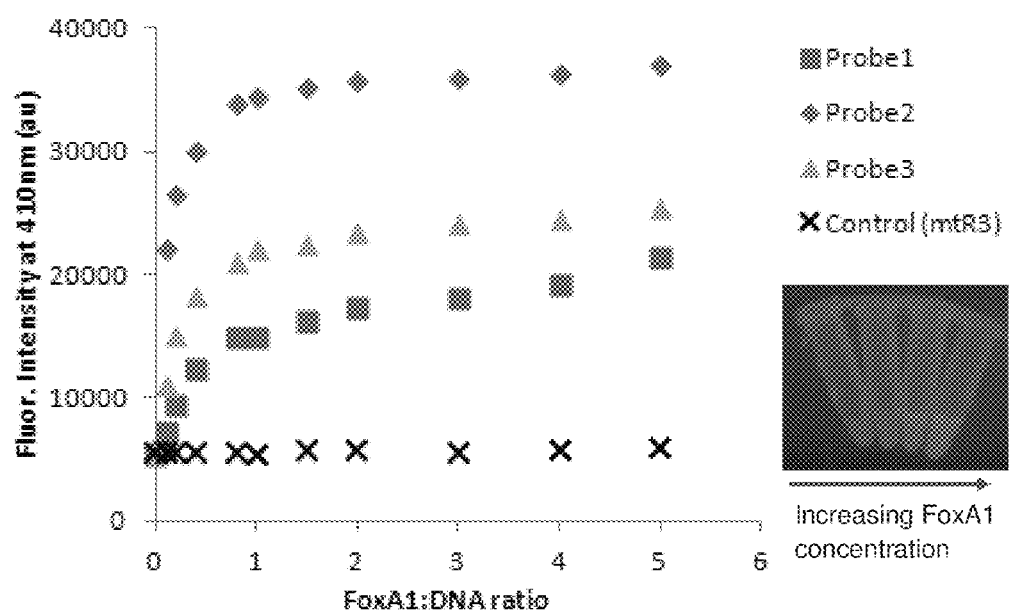
FIG. 11 is a graph showing the CCP-410 fluorescence titration curve of Probe1-, Probe2-, Probe3-, and control (mtR3)-AuNP with FoxA1. Inset shows the progressive recovery of the initially quenched fluorescence of CCP-410 by Probe2-AuNP.

The advantage of using cationic CP in the assay is that it relies on fluorescence turn-on as the signal read-out, which is more convenient for direct visual detection (FIG. 11 inset).

Example 7: Summary of CP Properties

Based on the above examples, any CPs of distinct charge and emission wavelength may be used to construct the AuNP-CP hybrid sensor for detecting both positive and negative charged proteins and proteins of unknown charge. Table 5 summarizes different CP and its applicability:

TABLE 5

Summary on the applicability of different CPs for dsDNA-AuNP assay.

| Type of CP | Degree of CP emission spectra overlapping with AuNP absorbance spectra | Dominant interaction with DNA | Protein that can be studied optimally | Reporting method (fluorescence signal) |
|---|---|---|---|---|
| Anionic (−) | Small | Hydrophobic | (+) charge | Quenching |
| Anionic (−) | Large | Hydrophobic | (+) & (−) charge | Quenching or recovery |
| Cationic (+) | Small | Electrostatic | (+) charge | Recovery |
| Cationic (+) | Large | Electrostatic | (+) charge | Recovery |

It should be noted that this assay is not limited to AuNPs being used as the fluorescence quencher. Silver nanoparticles (AgNPs) or silver/gold nanoparticle alloys (Au/Ag NP alloys) can also be utilized for similar purpose. Therefore, by choosing the suitable combination of metal NPs and CPs, customization of different types of protein and reporting methods is possible, particularly when fluorescence recovery is the method of choice.

Example 8: Measuring Binding Constant ($K_d$)

Qualitatively, the affinity of FOxA1 to different DNA probes can be identified by the degree of change in fluorescence intensity. For measuring the binding affinity constant $K_d$, protein titration was conducted using protein:DNA molar ratios of 0:1 to 5:1. That is, in a 50 nM solution of dsDNA-AuNPs, protein was added to achieve a concentration of 0-250 nM. The respective fluorescence intensity of the subsequent CP emission was recorded and compared with a control reaction containing no protein (FIG. 12).

Based on the relationship between protein concentration and fluorescence intensity, the binding constant, $K_d$, can be calculated using the equation:

$$(F_0-F)/(F-F_{sat})=([protein]/K_d)^n.$$

Figure 12:
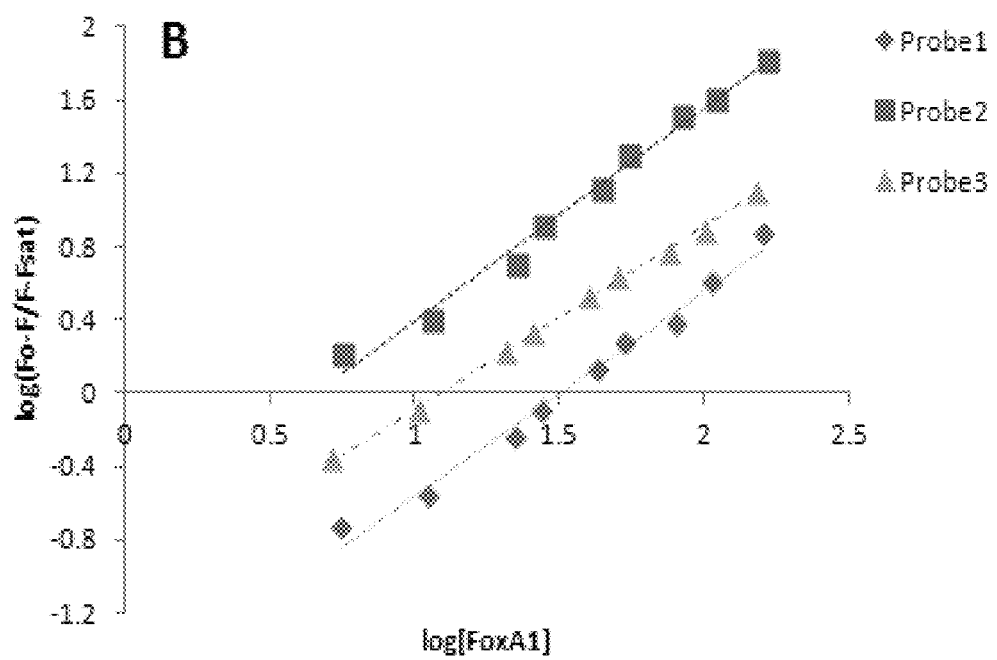
FIG. 12 is a graph showing the logarithmic plot of log $[(F_0-F)/(F-F_{sat})]$ vs. log [FoxA1] for deducing the binding constant ($K_d$) and binding stoichiometry between ACP-430 and FoxA1.

As shown in FIG. 12, the $K_d$ was obtained by plotting log $[(F_0-F)/(F-F_{sat})]$ versus log [protein], where F, $F_0$ and $F_{sat}$ are the relative fluorescence intensities in the presence of protein, in the absence of protein and in protein saturation, respectively. The value of log [protein] at log $[(F_0-F)/(F-F_{sat})]=0$ equals to the logarithm of the $K_d$. The slope, n, is the binding stoichiometry of protein to DNA.

The $K_d$ values obtained from the current fast assay method and conventional Electrophoretic Mobility Shift Assay (EMSA) and Fluorescence Anisotropy (FA) measurement are given in Table 6.

TABLE 6

Binding constant ($K_d$) of FoxA1 and AP-2γ measured with EMSA, FA and the CP/dsDNA-AuNP hybrid sensor

| DNA | FoxA1 | | | AP-2γ | |
|---|---|---|---|---|---|
| Sequences | Probe1 | Probe2 | Probe3 | wtR3 | mtR3 |
| EMSA | 458.72 ± 117.90 | 47.82 ± 5.45 | 241.66 ± 55.24 | 139.02 | N.A. |
| FA | 230.51 ± 34.07 | 16.03 ± 3.57 | 28.94 ± 6.49 | 50.62 ± 14.16 | 293 ± 111 |
| CP/dsDNA-AuNPs hybrid sensor (ACP-430) | 31.26 ± 4.41 | 4.47 ± 0.20 | 12.47 ± 1.09 | 12.39 ± 0.67 | 53.13 ± 4.04 |
| CP/dsDNA-AuNPs hybrid sensor (ACP-560) | 32.87 ± 4.04 | 5.76 ± 0.80 | 14.80 ± 1.51 | 14.63 ± 0.48 | 54.76 ± 1.34 |
| CP/dsDNA-AuNPs hybrid sensor (CCP-410) | 34.13 ± 3.48 | 5.02 ± 0.65 | 12.37 ± 0.40 | 12.97 ± 1.40 | 50.40 ± 3.15 |

From the EMSA and FA methods, it was shown that Probe2 (ideal sequence for FoxA1) has the highest binding affinity to FoxA1, followed by Probe3 (mutated at flank region) and Probe1 (mutated at the center region). Importantly, the currently developed assay shows the same affinity trend for FoxA1 as EMSA and FA, but the observed $K_d$ is generally lower. Such differences are common and expected since different measurement methods rely on different principles. However, the relative affinity as measured is consistent between all methods used. Interestingly, the absolute $K_d$ values of the currently developed method and FA are similar. This can be attributed to the fact that FA and the currently developed method are similar in that they are both homogenous phase complex formation assay methods.

The higher sensitivity (lower $K_d$) of the currently developed method may be attributed to the combination of the CP and spherical AuNPs used in the assay. The main advantage of using CPs as an optical probe compared to small molecules in bio-sensing is the possibility of multiple interaction points of the CP chain and a collective response that enhances the sensor signal. This is thought to be possible by the delocalized electron structure of the CP that facilitates efficient interactions with DNA molecules. Furthermore, AuNPs are excellent quenchers of fluorescence, as they are capable of receiving energy or electron transfer from the excited CP carriers over long distances.

Since the AuNP has a 3D structure, it could enhance the sensitivity of the assay by not spatially restricting the interaction. This is supported by the fact that, in addition to $K_d$, the slope of the logarithmic plot shown in FIG. 12 gave n~1, suggesting that FoxA1 bound to DNA in approximately a 1:1 ratio.

According to the $K_d$ value measured by the current method and FA, FoxA1 can bind to FoxA1 site (Probe2 and Probe3) efficiently (with higher affinity) when the core consensus sequence C/AAAC/T is preserved. Changing the flanking sequence (in Probe3) only leads to a slight decrease in affinity. On the other hand, the affinity drops significantly for Probe1 which is a 'T' to 'C' variant of Probe2 in the core binding sequence. The current experimental setup can differentiate between changes in the FoxA1 binding affinity by subtly altering the FoxA1 binding sequence. Therefore, this hybrid assembly can be potentially employed to determine the effect of modifications on risk loci on FoxA1 function and transcription.

$K_d$ measured using ACP-560 are reported in Table 6, which closely agrees with the values calculated previously with ACP-430. CCP-410 was also employed for fast screening of proteins and was used to determine the $K_d$ of FoxA1 (FIG. 11). The $K_d$ (Table 6) determined using the CCP-410 agreed with the $K_d$ measured with the two anionic CPs, ACP-430 and ACP-560. Further, not only was the $K_d$ in agreement, the stoichiometry of binding (n) deduced using the cationic CP supported the previous findings using ACP-430 that FoxA1 bound as a monomer with the DNA.

Example 9: Measuring AP-2γ-DNA Interactions Using CPs

The assay was also used to study a second transcription factor, AP-2γ (pI~7.8), to test the applicability of the method. wtR3 and mtR3 were used as the probe DNA sequences (Table 2). Similar to FoxA1, Ap-2γ binding was detected as either further quenching of fluorescence for ACP-430 or fluorescence recovery for CCP-410. From the relative decrease and increase in fluorescent intensity of CP with increasing concentration of AP-2γ, the binding affinity $K_d$ and n were determined. Similarly to FoxA1, the measured $K_d$ for AP-2γ followed a similar trend as the values calculated using FA (Table 6). The results suggested that AP-2γ bound stronger to wtR3 than to mtR3, as expected, as wtR3 has a stronger affinity for AP2γ than mrR3. The wtR3 probe contains palindromic sequences, 5'-GCCN$_3$GCC-3', which appears to be the core recognition elements for AP-2γ binding site. When the base was mutated to their purine and pyrimidine counterparts, AP-2γ binding affinity was affected drastically.

The finding that AP-2γ binds to a palindromic recognition sequence implies that AP-2γ may interact with DNA as a multimer. Moreover, the region of AP-2γ required for DNA binding is relatively large and suggests that, in addition to direct DNA contact, protein-protein contact between multiple AP-2γ molecules may help to stabilize the protein-DNA interaction. Based on the current assay, the slope of the plot was found to be −2, which confirms that AP-2γ binds to DNA as dimer. This result is in agreement with the previous findings for AP-2γ, where they were shown to exist as stable dimmers in solution and would lose the ability to bind DNA if the proteins did not dimerise.

Example 8: Screening Ligand Inhibition of Interaction

Some organic molecules can bind to proteins and change their DNA binding properties. Identification and characterization of small organic molecules that inhibit or weaken protein binding to DNA may lead to the discovery of new therapeutic drugs. The ability of 9 ligands (2 positive (inhibitor) and 7 negative (non-inhibitors)), selected from the NCI compound library (Table 3), at disrupting interaction between the transcription factors FoxA1 and AP-2γ and their respective binding DNA sequences were tested using the CPs. A positive ligand refers to a ligand that can inhibit protein binding to DNA, while a negative ligand is a ligand that does not interrupt the binding. It must be clearly understood that a particular ligand can bind strongly (with high affinity) to a certain protein but not inhibit the subsequent protein binding to DNA and vice versa. The main objective of this assay is to screen ligands that can interrupt protein binding to DNA regardless of their affinity to the protein.

The proteins and each ligand were mixed at a ratio of 1:8 for 10 min. The protein-ligand pre-incubation solution was then mixed with dsDNA-AuNP and further incubated for 20 mins. The CP was then added as the last step. Positive and negative controls were also prepared, where the positive control was dsDNA-AuNP incubated with protein without ligand, and the negative control was dsDNA-AuNPs incubated without any protein added.

Figures 13A, 13B:
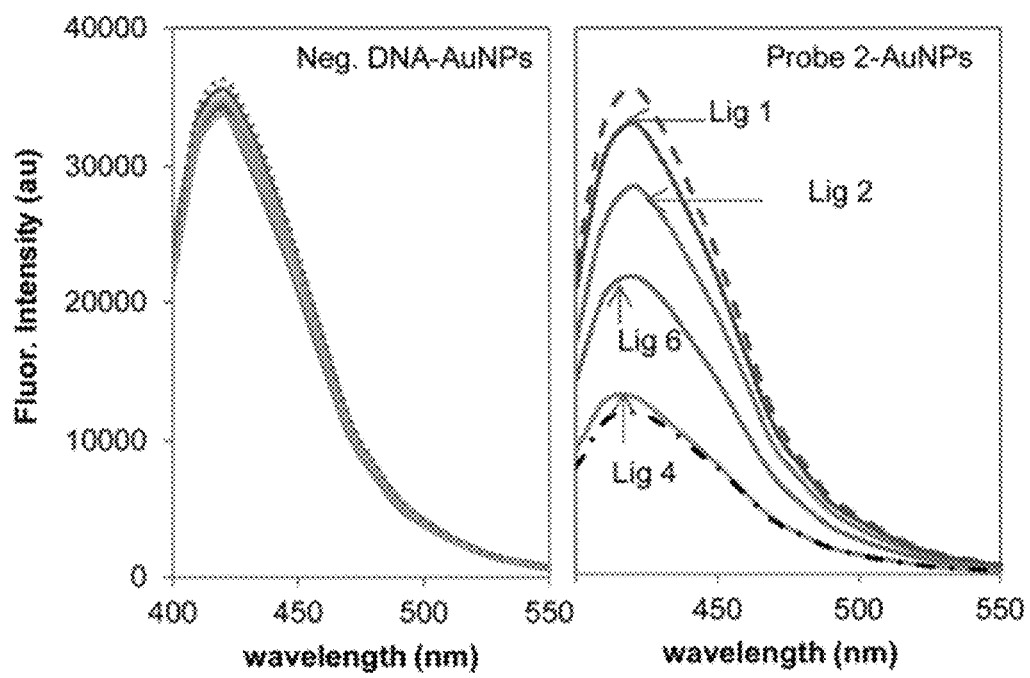
FIG. 13(A) is a graph showing the detection of ligand effect on FoxA1 binding to a negative control DNA (mtR3)-AuNPs using ACP-430.
FIG. 13(B) is a graph showing the detection of ligand effect on FoxA1 binding Probe2-AuNP using ACP-430.
Figures 14A, 14B:
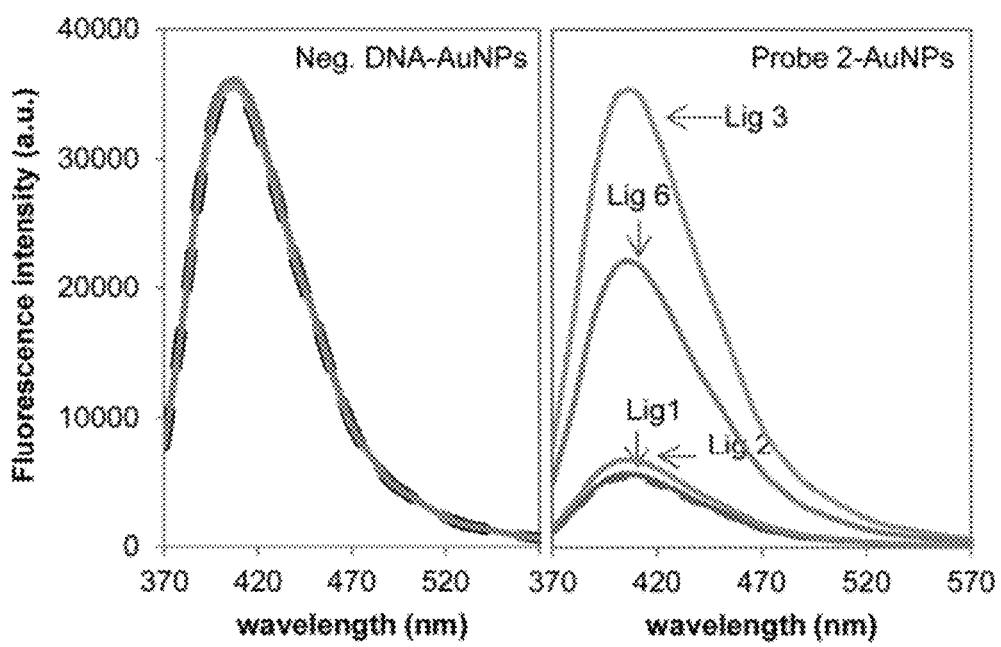
FIG. 14(A) is a graph showing the detection of ligand effect on FoxA1 binding to a negative control DNA (mtR3)-AuNPs using CCP-410.
FIG. 14(B) is a graph showing the detection of ligand effect on FoxA1 binding Probe2-AuNP using CCP-410.

FIGS. 13 and 14 show examples for FoxA1 and a few ligands detected by ACP-430/Probe2-AuNP (FIG. 13(B)) and CCP-410/Probe2-AuNP (FIG. 14(B)) sensors, with the negative control DNA-AuNP as reference (FIG. 13(A) and FIG. 14(A), respectively). The cationic CP has the opposite trend compared to the anionic CP, with the negative and positive controls having the lowest and highest fluorescence intensities, respectively. With both polymers, ligands 1 and 2 are found substantially inhibiting FoxA1-DNA binding. The respective CP emission is very similar to the cases where no protein is added. Other ligands, i.e. ligands 3 and 4, show negligible effect. The polymer emission is close to the case where FoxA1 is added without any ligands. Ligand 6 is found to inhibit FoxA1 binding to a partial degree. The same partial inhibition is observed for ligands 7 and 8, enervates FoxA1 binding affinity but not as effective as ligands 1 and 2.

Figure 15A:
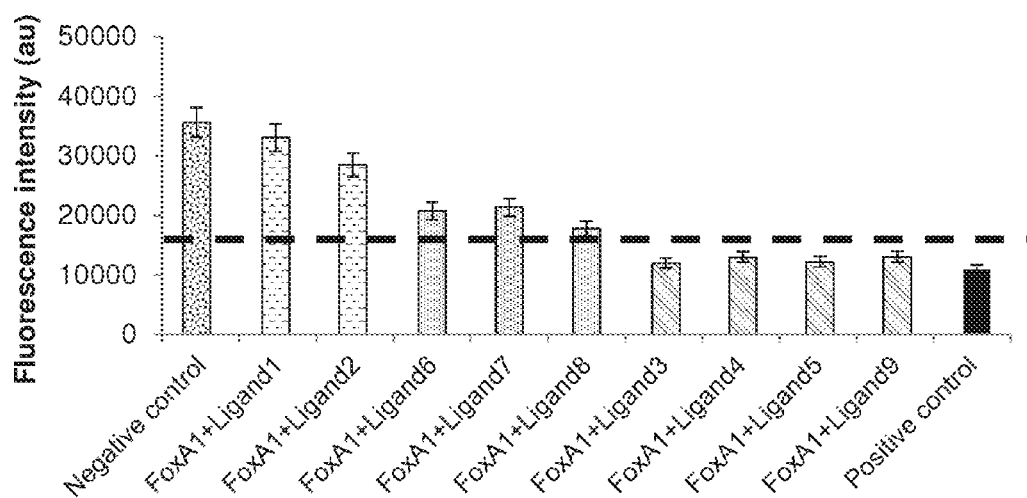
FIG. 15(A) is a graph showing the ligand screening for FoxA1 with the 9 ligands shown in Table 3. Dotted lines are for eye guidance. Positive, intermediate and negative ligands are labeled as red, green and purple bars respectively.
Figure 15B:
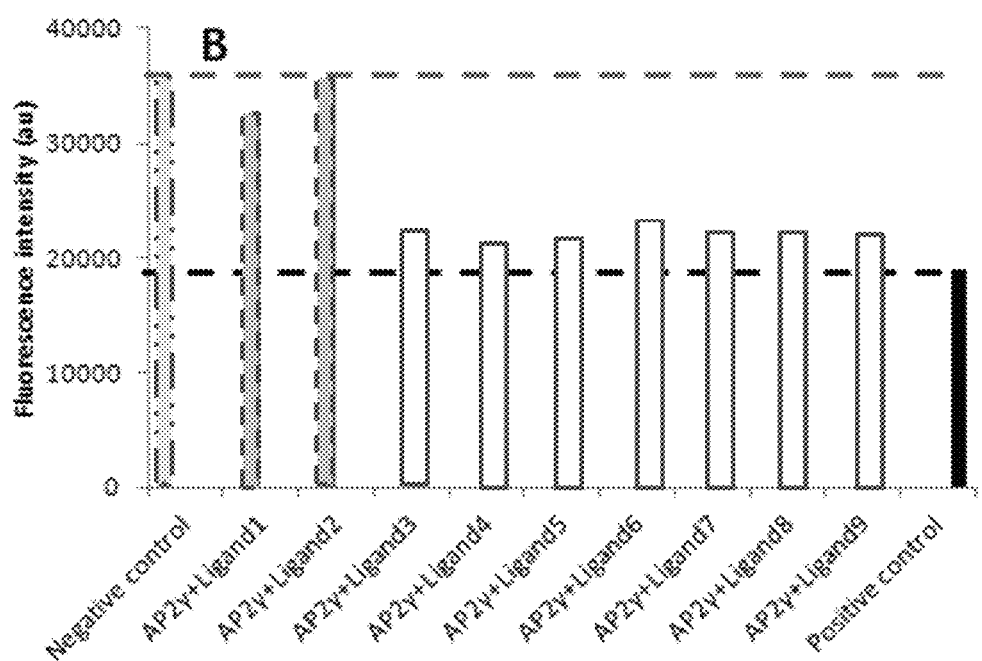
FIG. 15(B) is a graph showing the ligand screening for AP-2γ with the 9 ligands shown in Table 3. Dotted lines are for eye guidance. Positive, intermediate and negative ligands are labeled as red, green and purple bars respectively.
Figure 16:
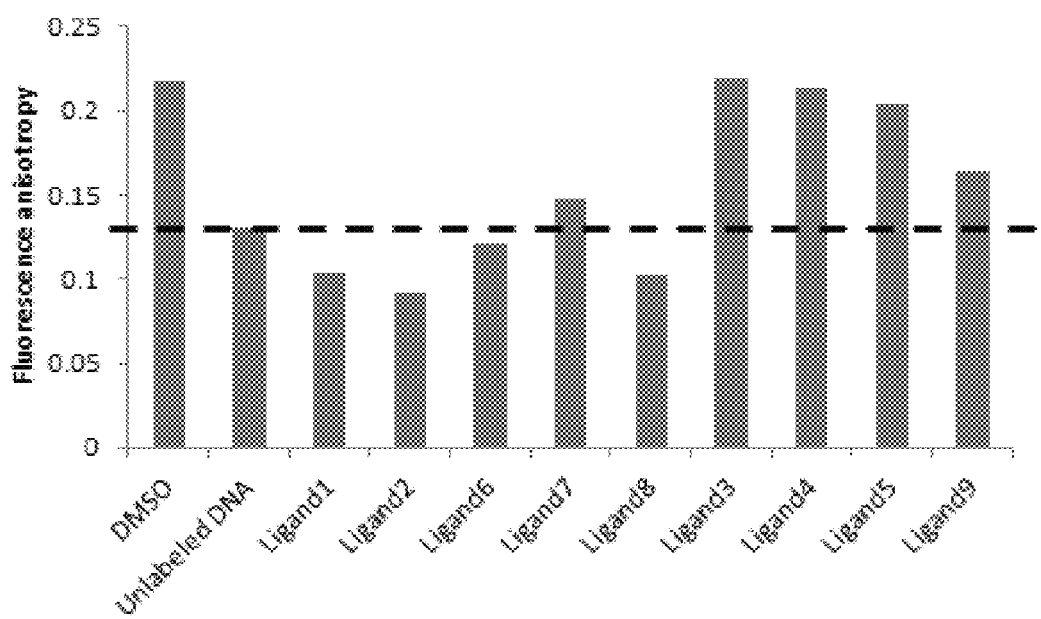
FIG. 16 is a graph showing ligand inhibition screening on FoxA1 as measured by fluorescence anisotropy (FA).

FIGS. 15 and 16 show the ligand inhibition tests for all 9 ligands by the ACP-430/Probe2-AuNP hybrid sensor and the traditional FA that relies on fluorescence labelled DNA. For the FA measurements (FIG. 16), the dashed line is the cut off value to determine any inhibition on FoxA1 binding to DNA, where ligands with values <0.13 are considered to be positive ligands. When FoxA1 binds to FAM-labelled Probe2, the overall size of the molecule increases. This will hamper the capability of FAM-Probe2 to rotate freely. The sluggish motion is seen as increase in fluorescence anisotropy of the FoxA1-Probe2 entity against the free Probe2. Successful ligand inhibition (by ligands 1 and 2 for example) is detected as a lower fluorescence anisotropy value, and vice versa. In the presence of FoxA1 (FIG. 15(A)) and AP-2γ (FIG. 15(B)), the fluorescence is highly quenched because protein binding lowers the overall DNA charge and then recruits more anionic CP to the surface of AuNPs. Positive ligands inhibit protein binding to DNA, thus is expected to behave in a comparable manner to the negative control.

For the 9 ligands tested, the FA result agrees well with the outcome concluded from the current assay. In the presence of ligands 3, 4, 5 and 9, FoxA1 can retain its binding capability with DNA, similarly to when no ligands are introduced. Both ligands 1 and 2 are classified as positive ligands for both proteins. Ligands 6 to 8 partially inhibited (intermediate ligand) and ligands 3 to 5 and 9 did not exert any significant influence on the FoxA1-Probe2 binding. Ligands 3 to 9 can be categorized as negative ligands due to the little or no impact they had on AP-2γ binding to wtR3.

APPLICATIONS

The disclosed sensor and method may be useful for screening a wide variety of nucleic acid-protein interactions.

The disclosed sensor and method may be useful in determining the presence or absence of nucleic acid-protein interactions.

The disclosed sensor and method may be useful for determining the $K_d$ of the nucleic acid-protein interaction.

The disclosed sensor and method may be useful for determining the stoichiometric ratio of the nucleic acid-protein ratio.

The disclosed sensor and method may lead to the discovery of new therapeutic drugs.

The disclosed sensor and method may be useful in the identification and characterization of small organic molecules that inhibit or weaken protein binding to DNA.

The disclosed method may be a simple, rapid and sensitive method for determining nucleic acid-protein interactions.

The disclosed sensor and method may be useful in developing an assay kit that is non-hazardous and does not require the use of expensive equipment or consumables.

The disclosed sensor and method may be useful in an alternative assay kit to what is currently available, as a safer and less expensive, yet simple and sensitive assay kit for detecting nucleic acid-protein interactions.

The disclosed sensor and method may be useful in studying protein quality in their ability to bind nucleic acid molecules.

The disclosed sensor and method may be useful in determining the quality of the protein. That is, the extent of denaturation or proper folding of a protein may be determined by using the sensor and method to study the nucleic-acid protein interaction.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A sensor for sensing nucleic acid-protein interactions, comprising:
   a. a noble metal nanoparticle (NP);
   b. a first single stranded nucleic acid molecule bonded onto the NP;
   c. a second, single stranded nucleic acid molecule, which is partially or completely complementary to the first nucleic acid molecule and is hybridized to the first nucleic acid molecule, to form a double stranded nucleic acid molecule capable of binding with a protein in an aqueous solution; and
   d. an enhanceable or quenchable fluorescent conjugated polymer (CP), wherein the conjugated polymer is a polymer of a structure selected from the group consisting of:

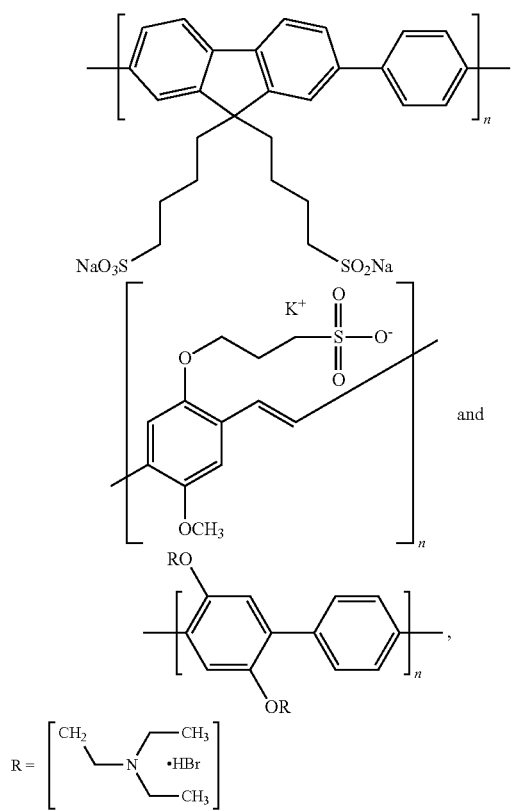

wherein the nucleic acid and the protein are not labelled with a dye, and wherein a fluorescence of the fluorescent conjugated polymer is enhanced or quenched as a result of energy transfer and/or electron transfer between the noble metal nanoparticle and the fluorescent conjugated polymer.

2. The sensor according to claim 1, wherein the fluorescence of the CP is quenchable by dynamic quenching.

3. The sensor according to claim 1, wherein the CP has a charge.

4. The sensor according to claim 3, wherein the CP is a charged conjugated polyelectrolyte (CPE).

5. The sensor according to claim 1, wherein the CP has "n" repeating units and the "n" value is in the range of 3 to 100.

6. The sensor according to claim 1, wherein the NP is a metal selected from the group consisting of gold (Au), silver (Ag), platinum (Pt), ruthenium (Ru) and any alloy thereof.

7. The sensor according to claim 6, wherein the NP is gold (Au) NP (AuNP).

8. The sensor according to claim 7, wherein the NP has a diameter in the range of 10 nm to 70 nm.

9. The sensor according to claim 8, wherein the fluorescence of the CP is quenched.

10. The sensor according to claim 9, wherein the fluorescence of the CP is restored when a positively charged protein or a negatively charged protein binds to the nucleic acid molecule bonded onto the NP.

11. The sensor according to claim 9, wherein the fluorescence of the CP is further quenched when a positively charged protein or a negatively charged protein binds to the nucleic acid molecule bonded onto the NP.

12. The sensor according to claim 7, wherein the NP has a diameter in the range of 80 nm to 200 nm.

13. The sensor according to claim 12, wherein the fluorescence of the CP is enhanced.

14. The sensor according to claim 13, wherein the fluorescence of the CP is quenched when a positively charged protein or a negatively charged protein binds to the nucleic acid molecule bonded onto the NP.

15. The sensor according to claim 13, wherein the fluorescence of the CP is further enhanced when a positively charged protein or a negatively charged protein binds to the nucleic acid molecule bonded onto the NP.

16. The sensor according to claim 1, wherein the first single stranded nucleic acid molecule is covalently bonded onto the NP.

17. The sensor according to claim 1, wherein the mole ratio of double stranded nucleic acid:NP is in the range of 90:1 to 100:1.

18. The sensor according to claim 1, wherein the single stranded nucleic acid molecule is selected from the group consisting of deoxyribonucleic acid (DNA), ribonucleic acid (RNA), small interfering RNA (siRNA), peptide nucleic acid (PNA) and locked nucleic acid (LNA).

19. The sensor according to claim 1, wherein the protein is negatively charged or positively charged.

20. The sensor according to claim 19, wherein the protein is a nucleic acid binding protein.

21. The sensor according to claim 20, wherein the nucleic acid binding protein is selected from the group consisting of Forkhead box protein A1 (FoxA1), Activating enhancer binding protein 2 gamma (AP-2γ), Estrogen receptor alpha (ERα), Estrogen receptor beta (ERβ) and specificity protein 1*(SP1).

22. The sensor according to claim 1, wherein the double stranded nucleic acid molecule comprises a protein recognition sequence.

23. The sensor according to claim 22, wherein the protein recognition sequence is 5'-GT ACT GT AAAT AAAACT-3' (SEQ ID NO:3) hybridized to 5'-AGTTTTATTTACAG-TAC-3' (SEQ ID NO:4) or 5' AAAGTGCCCAGAGC-CCATG-3 (SEQ ID NO:7) hybridized to 5'-CATGGGCTCTGGGCACTTT-3' (SEQ ID NO:8).

24. A method for sensing nucleic acid-protein interactions, comprising the steps of:
 i. bringing an aqueous solution suspected to comprise or known to comprise a protein of interest with the sensor according to claim 1; and
 ii. detecting the presence or absence of a fluorescent signal to determine the nucleic acid-protein binding.

25. The method according to claim 24, wherein step (i) further comprises the step of contacting the protein with a double stranded nucleic acid molecule bonded onto a NP.

26. The method according to claim 25, wherein the contacting step is performed at a nucleic acid:protein mole ratio in the range of 50:1 to 1:50.

27. The method according to claim 24, wherein step (i) further comprises the step of contacting a CP with the protein-bound double stranded nucleic acid molecule bonded onto a NP.

28. The method according to claim 27, wherein the contacting step is performed at a CP: nucleic acid mole ratio in the range of 2:1 to 1:1.

29. The method of claim 24 for drug screening or detecting the impact of single nucleotide mutation on nucleic acid-protein interaction.

* * * * *

```
                          SEQUENCE LISTING

<160> NUMBER OF SEQ ID NOS: 10

<210> SEQ ID NO 1
    <211> LENGTH: 17
    <212> TYPE: DNA
    <213> ORGANISM: Artificial Sequence
    <220> FEATURE:
    <223> OTHER INFORMATION: Single Stranded DNA

<400> SEQUENCE: 1
cactttgttt gcaaagc                                                  17

<210> SEQ ID NO 2
    <211> LENGTH: 17
    <212> TYPE: DNA
    <213> ORGANISM: Artificial Sequence
    <220> FEATURE:
    <223> OTHER INFORMATION: Single Stranded DNA

<400> SEQUENCE: 2
gctttgcaaa caaagtg                                                  17

<210> SEQ ID NO 3
    <211> LENGTH: 17
    <212> TYPE: DNA
    <213> ORGANISM: Artificial Sequence
    <220> FEATURE:
    <223> OTHER INFORMATION: Single Stranded DNA

<400> SEQUENCE: 3
gtactgtaaa taaaact                                                  17

<210> SEQ ID NO 4
    <211> LENGTH: 17
    <212> TYPE: DNA
    <213> ORGANISM: Artificial Sequence
    <220> FEATURE:
    <223> OTHER INFORMATION: Single Stranded DNA

<400> SEQUENCE: 4
agttttattt acagtac                                                  17

<210> SEQ ID NO 5
    <211> LENGTH: 19
    <212> TYPE: DNA
    <213> ORGANISM: Artificial Sequence
```

```
<220> FEATURE:
<223> OTHER INFORMATION: Single Stranded DNA

<400> SEQUENCE: 5
tgccaagtaa atagtgcag                                              19

<210> SEQ ID NO 6
<211> LENGTH: 19
<212> TYPE: DNA
<213> ORGANISM: Artificial Sequence
<220> FEATURE:
<223> OTHER INFORMATION: Single Stranded DNA

<400> SEQUENCE: 6
ctgcactatt tacttggca                                              19

<210> SEQ ID NO 7
<211> LENGTH: 19
<212> TYPE: DNA
<213> ORGANISM: Artificial Sequence
<220> FEATURE:
<223> OTHER INFORMATION: Single Stranded DNA

<400> SEQUENCE: 7
aaagtgccca gagcccatg                                              19

<210> SEQ ID NO 8
<211> LENGTH: 19
<212> TYPE: DNA
<213> ORGANISM: Artificial Sequence
<220> FEATURE:
<223> OTHER INFORMATION: Single Stranded DNA

<400> SEQUENCE: 8
catgggctct gggcacttt                                              19

<210> SEQ ID NO 9
<211> LENGTH: 19
<212> TYPE: DNA
<213> ORGANISM: Artificial Sequence
<220> FEATURE:
<223> OTHER INFORMATION: Single Stranded DNA

<400> SEQUENCE: 9
aaagtattca gaatccatg                                              19

<210> SEQ ID NO 10
<211> LENGTH: 19
<212> TYPE: DNA
<213> ORGANISM: Artificial Sequence
<220> FEATURE:
<223> OTHER INFORMATION: Single Stranded DNA

<400> SEQUENCE: 10
catggattct gaatacttt                                              19
```